(12) United States Patent
Kageyama et al.

(10) Patent No.: US 10,183,022 B2
(45) Date of Patent: Jan. 22, 2019

(54) PHARMACEUTICAL COMPOSITION FOR TREATING ULCERATIVE COLITIS

(71) Applicant: EA Pharma Co., Ltd., Tokyo (JP)

(72) Inventors: Shunsuke Kageyama, Tokyo (JP); Yoshiki Goda, Tokyo (JP); Toshihiko Sugiura, Tokyo (JP)

(73) Assignee: EA Pharma Co., Ltd., Tokyo (JP)

( * ) Notice: Subject to any disclaimer, the term of this patent is extended or adjusted under 35 U.S.C. 154(b) by 0 days.

(21) Appl. No.: 15/471,745

(22) Filed: Mar. 28, 2017

(65) Prior Publication Data

US 2017/0196870 A1    Jul. 13, 2017

Related U.S. Application Data

(63) Continuation of application No. PCT/JP2015/059717, filed on Mar. 27, 2015.

(30) Foreign Application Priority Data

Sep. 29, 2014  (JP) ................. 2014-198681

(51) Int. Cl.
    *A61K 31/517*    (2006.01)
    *A61K 9/00*      (2006.01)
    *A61K 9/20*      (2006.01)

(52) U.S. Cl.
    CPC .......... *A61K 31/517* (2013.01); *A61K 9/0053* (2013.01); *A61K 9/20* (2013.01)

(58) Field of Classification Search
    CPC .................................................. A61K 31/517
    See application file for complete search history.

(56) References Cited

U.S. PATENT DOCUMENTS

| | | |
|---|---|---|
| 2003/0220268 A1 | 11/2003 | Makino et al. |
| 2006/0009476 A1 | 1/2006 | Kataoka et al. |
| 2006/0204572 A1 | 9/2006 | Higuchi et al. |
| 2006/0204574 A1 | 9/2006 | Ogawa et al. |
| 2006/0223836 A1 | 10/2006 | Makino et al. |
| 2007/0018172 A1 | 1/2007 | Takahashi et al. |
| 2008/0108637 A1 | 5/2008 | Fujita et al. |
| 2009/0319688 A1 | 12/2009 | Kataoka et al. |
| 2010/0137593 A1 | 6/2010 | Takahashi et al. |
| 2010/0204505 A1 | 8/2010 | Kataoka et al. |
| 2011/0009434 A1 | 1/2011 | Fujita et al. |
| 2011/0065918 A1 | 3/2011 | Makino et al. |
| 2011/0313154 A1 | 12/2011 | Kataoka et al. |
| 2012/0253041 A1 | 10/2012 | Makino et al. |
| 2013/0030013 A1 | 1/2013 | Aburatani et al. |
| 2013/0066072 A1 | 3/2013 | Kataoka et al. |
| 2014/0206705 A1 | 7/2014 | Kataoka et al. |
| 2016/0082009 A1 | 3/2016 | Aburatani et al. |

FOREIGN PATENT DOCUMENTS

| | | |
|---|---|---|
| WO | 02/16329 A1 | 2/2002 |
| WO | 2004/074264 A1 | 9/2004 |
| WO | 2005/046696 A1 | 5/2005 |
| WO | 2005/046697 A1 | 5/2005 |
| WO | 2005/051525 A1 | 6/2005 |
| WO | 2006/137450 A1 | 12/2006 |
| WO | 2008/062859 A1 | 5/2008 |
| WO | 2011/122619 A1 | 10/2011 |
| WO | 2011/122620 A1 | 10/2011 |

OTHER PUBLICATIONS

Halland et al.—"Small Macrocycles As Highly Active Integrin α2β1 Antagonists" *ACS Medicinal Chemistry Letters* 2014, 5, pp. 193-198.
Tilley "Very late antigen-4 integrin antagonists", *Expert Opin. Ther. Patents* (2008), 18(8), pp. 841-859.
Maruyama et al.—"An Orally Active Alpha-1 Integrin Antagonist Ajm300 Attenuates Inflammatory Cell Infiltration and Exacerbation of DSS-Induced Chronic Colitis in Rats" AGA Abstracts, A-229, S1598, 2007.
Yokoyama—"Special: Therapeutic Strategy for Ulcerative Colitis—From Standard Therapies to the Latest Information" (with partial English translation) Intestine, vol. 15, No. 3, 2011, (17 pages).
Watanabe et al.—"Special: New Therapeutic Strategy in Ulcerative Colitis X. Possibility in New Medical Therapy in the Future" (with partial English translation) Intestine, vol. 17, No. 2, 2013 (12 pages).
Suzuki—"The Current Status of the Development of Therapeutic Drug for Inflammatory Bowel Disease New Therapies Now", (with partial English translation) *medicina* vol. 45, No. 5, May 2008, (10 pages).

(Continued)

*Primary Examiner* — James D. Anderson
(74) *Attorney, Agent, or Firm* — Oblon, McClelland, Maier & Neustadt, L.L.P.

(57) ABSTRACT

Provided is a pharmaceutical composition for treating ulcerative colitis, comprising a compound represented by a formula (1) or a pharmaceutically acceptable salt thereof, wherein the compound or the pharmaceutically acceptable salt is administered in an amount of 600 mg or more per day to an ulcerative colitis patient.

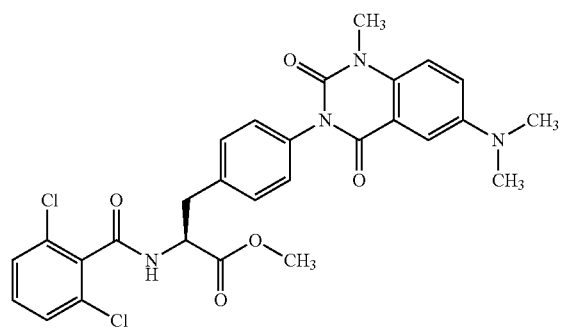

(1)

11 Claims, 6 Drawing Sheets

(56) References Cited

OTHER PUBLICATIONS

Hisamatsu et al.—"Ulcerative Colitis •Crohn's Disease • Topics Expectation of New Drug Therapy Based on Pathological Discoveries" (with partial English translation) Medical Practice vol. 29, No. 7, 2012,(15 pages).
Kihara New Oral α4 Integrin Inhibitor—A Novel Orally Active Alpha 4 Integrin Antagonist (with partial English translation) Medical Science Digest vol. 37(9), 2011 (15 pages).
Kougo—"New Therapies Delivered From Japan to the World"(with partial English translation) New Therapeutic Modalities from Japan to Global Field, vol. 64, No. 9, 2009 (18 pages).
Nakase et al.—"New Immunopathology and Target Therapy"(with partial English translation), Developments of New Target Therapies for Regulating Immune System of Inflammatory Bowel Disease, vol. 64, No. 9, 2009 (21 pages).
Hokari et al.—"Special/Today's Approach to Inflammatory Bowel Diseases—Pathogenesis and Pathophysiology of Inflammatory Bowel Disease from the Viewpoints of Lymphocyte Homing and Adhesion Molecule" Adult Diseases, 2010, vol. 40, No. 12 (24 pages).
Kougo et al.—"Current status of new drug development for inflammatory bowel disease" VI Medical Treatment for Inflammatory Bowel Disease, Nippon Rinsho, 2012, vol. 70, suppl.1, (17 pages).
Takazoe et al.—"S1066 Oral Alpha-$_4$ Integrin Inhibitor (AJM300) in Patients with Active Crohn's Disease—a Randomized, Double-Blind, Placebo-Controlled Trial", *Gastroenterology* May 2009, vol. 136, Issue 5, Supplement 1 (4 pages).
Sugiura et al.—"M1647 An Orally Active Alpha, Integrin Antagonist AJM300 Prevents the Development of Experimental Colitis Induced by Adoptive Transfer of IL-10 Deficient CD4+ T Cells in Mice", *Gastroenterology*, May 2009, vol. 136, Issue 5, Supplemental 1.
Thomas et al.—"Targeting leukocyte migration and adhesion in Crohn's disease and ulcerative colitis", *Inflammopharmacol* (2012), 20, pp. 1-18.
Sugiura et al.—"Oral treatment with a novel small molecule alpha 4 integrin antagonist, AJM300, prevents the development of experimental colitis in mice", *Journal of Crohn's and Colitis* (2013), 7, pp. 533-542.
Ghosh et al.—"Inhibition of Selective Adhesion Molecules in Treatment of Inflammatory Bowel Disease", *International Reviews of Immunology*. 31, pp. 410-427, 2012.
Lobatón et al.—"Review article: anti-adhesion therapies for inflammatory bowel disease", *Aliment Pharmacol Ther* 2014. 39, pp. 579-594.
Watanabe—"Treatment Strategy for Ulcerative Colitis", *Kaiyoseidaichouen chiryoshishin* (revised in 2012) (23 pages).
Toruner et al.—"Risk Factors for Opportunistic Infections in Patients with Inflammatory Bowel Disease", *Gastroenterology* 2008, 134, pp. 929-936.
Curkovic et al.—"Risks of Inflammatory Bowel Disease Treatment with Glucocorticosteroids and Aminosalicylates", *Digestive Diseases*. 2013, 31, pp. 368-373.
Rostholder et al.—"Outcomes after escalation of infliximab therapy in ambulatory patients with moderately active ulcerative colitis" *Ailment Pharmacol Ther* 2012, 35, pp. 562-567.
Gisbert et al.—"Loss of Response and Requirement of Infliximab Dose Intensification in Crohn's Disease—A Review" *The American Journal of Gastroenterology*, vol. 104, Mar. 2009, pp. 760-767.
Regueiro et al.—"Infliximab Dose Intensification in Crohn's Disease", *Inflamm Bowel Dis*, vol. 13, No. 9, Sep. 2007, pp. 1093-1099.
Schroeder et al.—"Coated Oral 5-Aminosalicylic Acid Therapy for Mildly to Moderately Active Ulcerative Colitis", *The New England Journal of Medicine*, vol. 317, No. 26, 1987 pp. 1625-1629.
Watanabe et al.—"AJM300, an Oral α4 Integrin Antagonist, for Active Ulcerative Colitis: A Multicenter, Randomized, Double-Blind, Placebo-Controlled Phase 2A Study", slide show and presentation and conference program from Digestive Disease Week2014, May 2014.
Ito et al.—"Oral Treatment with Novel Alpha4 Integrin Blocker, AJM300, is Efficacious in a Rat Model of DNBS-Induced Colitis", AGA Abstracts, A-200, S1360. 2005 (3 pages).
*Gastroenterology* vol. 146. Issue 5, Supplement 1, abstracts, May 2014.

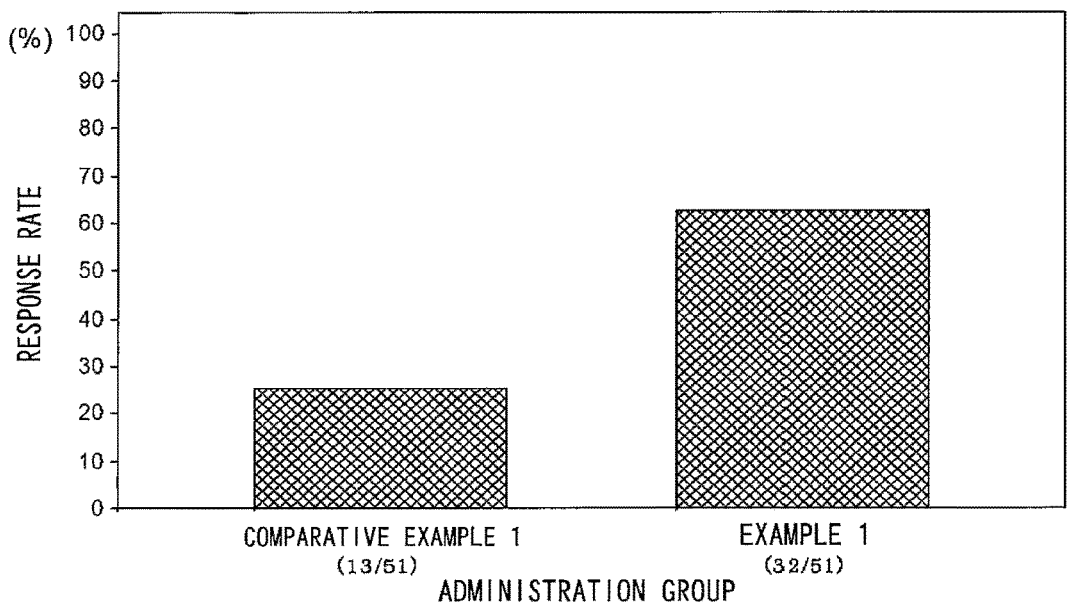
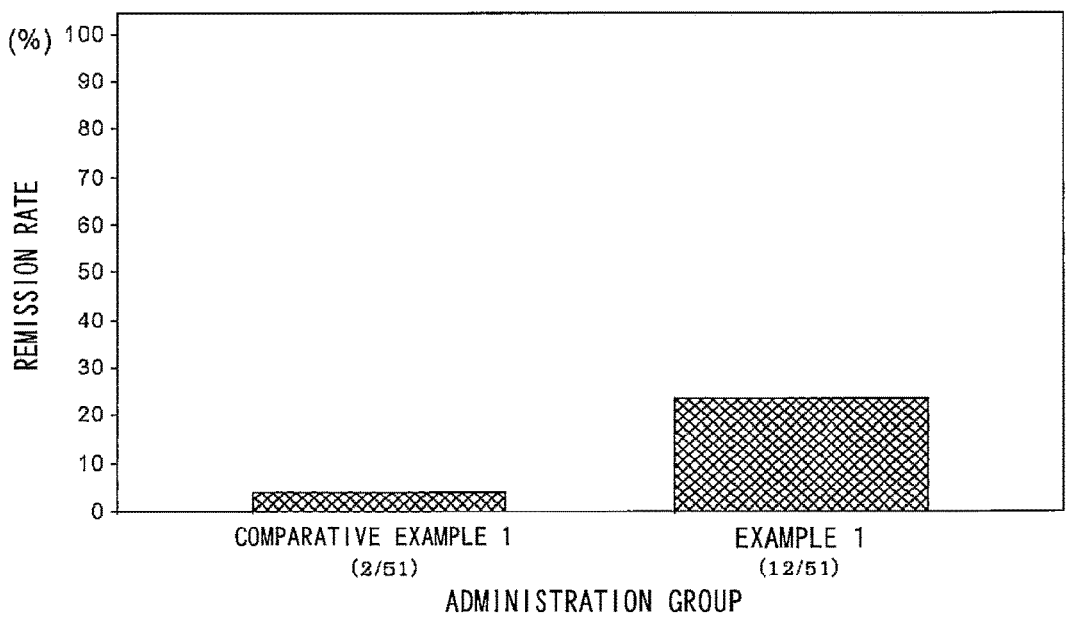

SUBSCORE FOR MUCOSAL FINDING OF MAYO SCORE

SUBSCORE FOR STOOL FREQUENCY OF MAYO SCORE

SUBSCORE FOR BLOODY STOOL OF MAYO SCORE

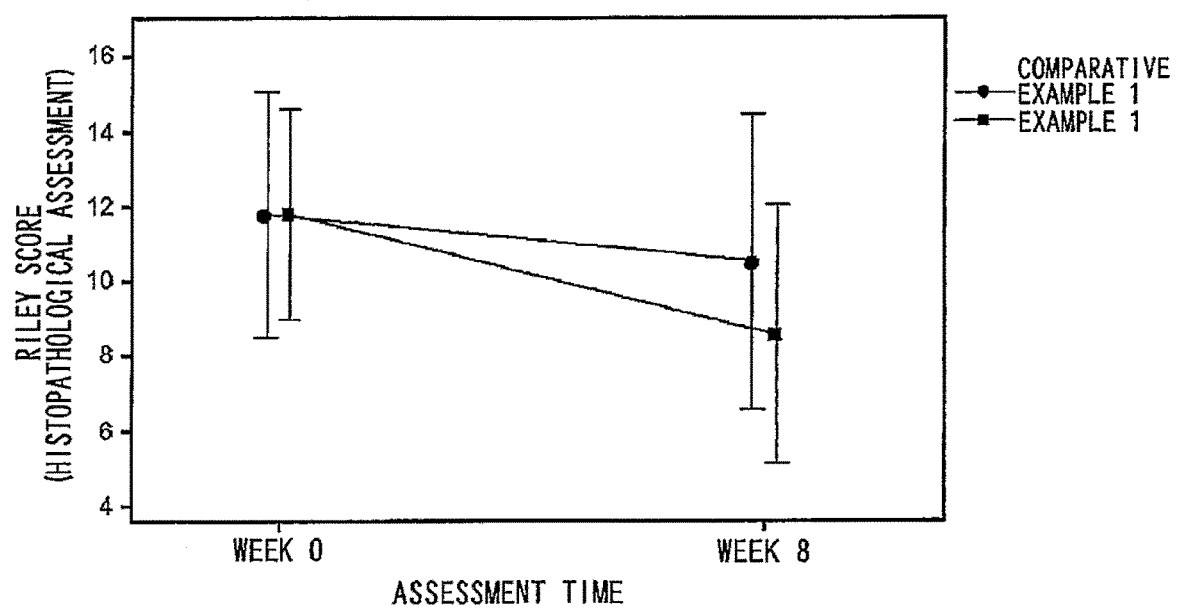

PHARMACEUTICAL COMPOSITION FOR TREATING ULCERATIVE COLITIS

CROSS REFERENCE TO RELATED APPLICATIONS

The present application is a continuation application of International patent application PCT/JP2015/059717, filed on Mar. 27, 2015, published as WO/2016/051828 on Apr. 7, 2016, the text of which is incorporated by reference, and claims the benefit of the filing date of Japanese application no. 2014-198681, filed on Sep. 29, 2014, the text of which is also incorporated by reference.

TECHNICAL FIELD

The present invention relates to a pharmaceutical composition useful as an agent for treating ulcerative colitis. Particularly, the present invention relates to a pharmaceutical composition for treating ulcerative colitis effectively for ulcerative colitis patients receiving a drug therapy of a 5-aminosalicylic acid preparation and/or a corticosteroid preparation.

BACKGROUND ART

Ulcerative colitis is an inflammatory disease of the large intestine that causes erosions and/or ulcers in the mucosa of the large intestine, and classified into mild, moderate, severe, and fulminant diseases according to the severity. Main symptoms of ulcerative colitis include diarrhea and bloody stool. In addition, ulcerative colitis often repeats an active stage during which the above symptoms appear, and a remission stage during which the above symptoms subside by a treatment.

A treatment guideline against ulcerative colitis recommends that an appropriate drug should be selected depending on the severity and the symptom of the disease, but the treatment is mainly given with a 5-aminosalicylic acid preparation (also referred to as 5-ASA preparation) and a corticosteroid preparation. In the standard treatment, an oral 5-ASA preparation is used alone or in combination with a topical preparation. Nevertheless, if the effect is insufficient, the remission is induced by a treatment with an oral corticosteroid preparation. A patient recognized as having resistance to or dependency on the corticosteroid preparation treatment is considered as a refractory case. For the treatment of such patients, apheresis, tacrolimus oral administration, azathioprine or 6-mercaptopurine (6-MP), or an anti-TNFα antibody preparation is selected (Non Patent Literature 1).

A 5-ASA preparation occasionally causes an allergic reaction with fever and diarrhea. For patients who cannot receive the standard treatment from the above reasons, there is a great need for a novel treatment option. Meanwhile, a corticosteroid preparation can be expected to exhibit a strong efficacy, but is well known to have a side-effect problem such as infectious diseases. The risk of infectious diseases from a 5-ASA preparation is at the same level as in the non-treatment, whereas a corticosteroid preparation has been reported to increase the risk by 3.3 fold. Furthermore, various side effects thereof are known such as hyperglycemia, adrenal gland disorder, and osteoporosis.

Additionally, since the apheresis is an extracorporeal circulation procedure, this puts a physically heavy burden and a long restraint on a patient. The tacrolimus oral administration has been reported to have serious side effects such as renal dysfunction and pancreatic dysfunction, so that a complicated trough level control is necessary through hospitalization or under a control comparable to the hospitalization. Hence, the tacrolimus oral administration is disadvantageous in that the burdens of the subject and medical staff are considerable even though the drug is an oral preparation. Infliximab intravenous infusion is known to cause antigenic infusion reaction and delayed type hypersensitivity in addition to a lethal side effect such as hepatosplenic T-cell lymphoma, one of malignant tumors. Moreover, there is a report that, among the administered patients, at most approximately 70% of the patients showed the loss of the response. A secondary failure is one of causes of the loss, and is a major problem (Non Patent Literatures 2 to 6).

CITATION LIST

Non Patent Literatures

Non Patent Literature 1: Mamoru Watanabe. Kaiyoseidaichouen chiryoshi shin (Treatment guideline against ulcerative colitis) (revised in 2012)

Non Patent Literature 2: Toruner M, Loftus E V Jr, Harmsen W S, Zinsmeister A R, Orenstein R, Sandborn W J, Colombel J F, Egan L J. Risk factors for opportunistic infections in patients with inflammatory bowel disease. Gastroenterology. 2008; 134: 929-36.

Non Patent Literature 3: Curkovic I, Egbring M, Kullak-Ublick G A. Risks of inflammatory bowel disease treatment with glucocorticosteroids and aminosalicylates. Dig Dis. 2013; 31: 368-73

Non Patent Literature 4: Rostholder E, Ahmed A, Cheifetz A S, Moss A C. Outcomes after escalation of infliximab therapy in ambulatory patients with moderately active ulcerative colitis. Aliment Pharmacol Ther. 2012; 35: 562-7.

Non Patent Literature 5: Gisbert J P, Panes J. Loss of response and requirement of infliximab dose intensification in Crohn's disease: a review. Am J Gastroenterol. 2009; 104: 760-7.

Non Patent Literature 6: Regueiro M, Siemanowski B, Kip K E, Plevy S. Infliximab dose intensification in Crohn's disease. Inflamm Bowel Dis. 2007; 13: 1093-9.

SUMMARY OF INVENTION

Technical Problem

There are many patients on whom the use of a 5-ASA preparation and/or a corticosteroid preparation has an insufficient effect or who are intolerant to the use of a 5-ASA preparation and/or a corticosteroid preparation, and whose symptoms are not relieved. There is a medical need for the development of a drug which effectively acts on such patients.

Solution to Problem

As a result of conducting intensive study to solve the above-described problems, the present invention has revealed that a compound represented by a formula (1) or a pharmaceutically acceptable salt thereof effectively acts on ulcerative colitis patients, particularly ulcerative colitis patients receiving a drug therapy of a 5-ASA preparation and/or a corticosteroid preparation.

Specifically, the present invention includes the following inventions.

[1] A pharmaceutical composition for treating ulcerative colitis, comprising a compound represented by the following formula (1) or a pharmaceutically acceptable salt thereof, wherein
the compound or the pharmaceutically acceptable salt is administered as an active ingredient in an amount of 600 mg or more per day to an ulcerative colitis patient.

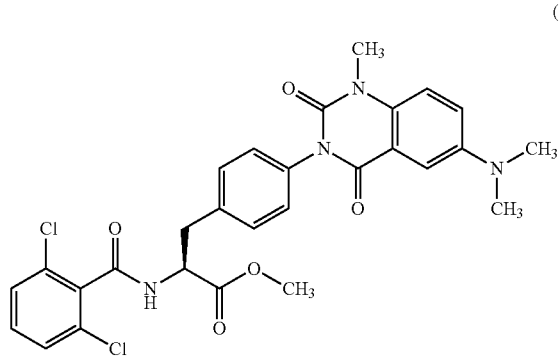

(1)

[2] The pharmaceutical composition according to [1], wherein the compound or the pharmaceutically acceptable salt is administered as an active ingredient in an amount of 600 mg to 9000 mg per day to an ulcerative colitis patient.
[3] The pharmaceutical composition according to [1] or [2], wherein the patient is an ulcerative colitis patient receiving a drug therapy of a 5-aminosalicylic acid preparation and/or a corticosteroid preparation.
[4] The pharmaceutical composition according to any one of [1] to [3], wherein the patient is an ulcerative colitis patient in an active stage on whom a drug therapy of a 5-aminosalicylic acid preparation and/or a corticosteroid preparation has an insufficient effect, or who is intolerant to the drug therapy.
[5] The pharmaceutical composition according to any one of [1] to [4], which is an oral preparation.
[6] The pharmaceutical composition according to any one of [1] to [5], wherein the compound or the pharmaceutically acceptable salt is administered 1 to 5 times a day.
[7] The pharmaceutical composition according to any one of [1] to [6], wherein the compound or the pharmaceutically acceptable salt is administered 3 times a day at a dose of 200 mg or more per administration.
[8] The pharmaceutical composition according to [7], wherein the compound or the pharmaceutically acceptable salt is administered 3 times a day at a dose of 200 mg to 3000 mg per administration.

Advantageous Effects of Invention

The use of the pharmaceutical composition of the present invention makes it possible to effectively treat ulcerative colitis patients, particularly ulcerative colitis patients receiving a drug therapy of a 5-ASA preparation and/or a corticosteroid preparation.

BRIEF DESCRIPTION OF DRAWINGS

FIG. 1 is a graph showing responserates of administration groups in Example 1 and Comparative Example 1.
FIG. 2 is a graph showing remission rates of the administration groups in Example 1 and Comparative Example 1.
FIG. 11 is a graph showing changes over time in Riley scores of the administration groups in Example 1 and Comparative Example 1.

DESCRIPTION OF EMBODIMENTS

Figure 3:
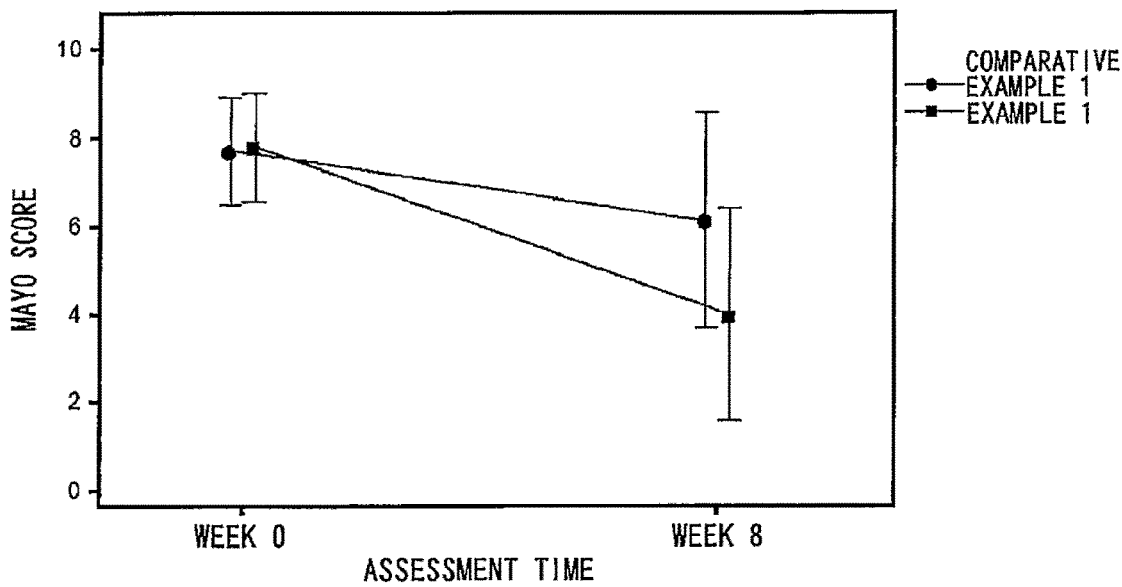
FIG. 3 is a graph showing changes over time in Mayo scores of the administration groups in Example 1 and Comparative Example 1.

A pharmaceutical composition of the present invention comprises, as an active ingredient, a compound represented by the following formula (1) (hereinafter, also referred to simply as compound (1)) or a pharmaceutically acceptable salt thereof. The compound (1) or the pharmaceutically acceptable salt is capable of quite effectively acting on ulcerative colitis patients, preferably ulcerative colitis patients receiving a drug therapy of a 5-ASA preparation and/or a corticosteroid preparation, and particularly, ulcerative colitis patients in an active stage on whom a drug therapy of a 5-ASA preparation and/or a corticosteroid preparation has an insufficient effect, or who are intolerant to the drug therapy.

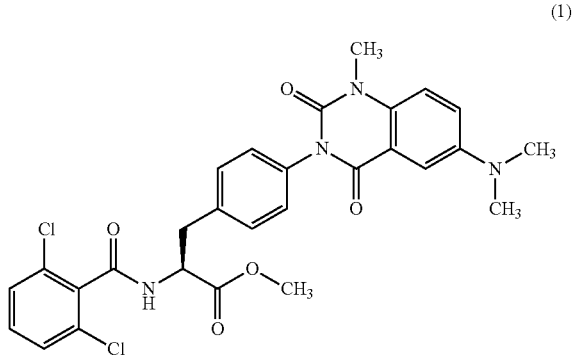 [SMILES: COC(=O)[C@H](Cc1ccc(-n2c(=O)c3cc(N(C)C)ccc3n(C)c2=O)cc1)NC(=O)c1c(Cl)cccc1Cl]

(1)

methyl(2S)-2-(2,6-dichlorobenzamide)-3-{4-[6-(dimethylamino)-1-methyl-2,4-dioxo-1,4-dihydroquinazolin-3(2H)-yl]phenyl}propanoate The compound (1) can be produced, for example, according to the methods described in International Publication No. WO02/16329 and International Publication No. WO2004/074264 (Example 1).

Examples of the pharmaceutically acceptable salt of the compound (1) include salts with inorganic acids (such as hydrochloric acid, sulfuric acid, and phosphoric acid), salts with organic carboxylic acids (acetic acid, citric acid, benzoic acid, maleic acid, fumaric acid, tartaric acid, and succinic acid), and salts with organic sulfonic acids (such as methanesulfonic acid and p-toluenesulfonic acid).

The method for forming the salt includes: a method in which the compound (1) is mixed with a necessary acid or base at an appropriate amount ratio in a solvent or a dispersant; and a method in which the compound (1) in another salt form is converted by cation exchange or anion exchange.

Moreover, the compound (1) of the present invention also includes solvates, for example, hydrates, alcohol adducts, and the like, of the compound (1).

<Target Patients>

The patients targeted in the present invention are ulcerative colitis patients, particularly ulcerative colitis patients receiving a drug therapy of a 5-ASA preparation and/or a corticosteroid preparation. Above all, preferable are ulcerative colitis patients in an active stage on whom a drug therapy of an oral 5-ASA preparation and/or an oral corticosteroid preparation has an insufficient effect or who are intolerant to even a drug therapy of an oral 5-ASA preparation and/or an oral corticosteroid preparation.

The 5-ASA preparation is a collective term for drugs containing 5-ASA and a derivative thereof as active ingredients. Examples of the active ingredients include mesalazine, salazosulfapyridine, olsalazine, and balsalazide. Drugs containing mesalazine as an active ingredient includes Pentasa (registered trademark), Asacol (registered trademark), Lialda (registered trademark), Salofalk (registered trademark), and the like.

The corticosteroid preparation is a collective term for drugs containing corticosteroid as an active ingredient. Examples of the active ingredient include prednisolone, betamethasone, dexamethasone, hydrocortisone, triamcinolone, and budesonide.

Further, the patients targeted in the present invention are preferably moderate ulcerative colitis patients each having a Mayo score of 6 points or more but 10 points or less.

The "Mayo score" is an index for assessing the activity of ulcerative colitis, and a total value thereof is made up of four subscores ("stool frequency," "bloody stool," "mucosal finding," and "physician's global assessment"). Each of the subscores goes up to 3 points at most, and a "Mayo score" is assessed with 12 points in total. Higher points mean a higher severity of the disease. The Mayo score is widely used as a disease activity assessment index against ulcerative colitis in the latest clinical studies. Reference can be made to, for example, "Schroeder K W, Tremaine W J, Ilstrup D M. Coated oral 5-aminosalicylic acid therapy for mildly to moderately active ulcerative colitis. A randomized study. N Engl J Med. 1987; 317: 1625-9."

Furthermore, the patients targeted in the present invention are preferably patients each having a Mayo score with a "subscore for mucosal finding" of 2 points or more and a "subscore for bloody stool" of 1 point or more.

The "subscore for mucosal finding" is given from 0 to 3 points depending on the state of the large intestinal mucosa observed in an endoscopic examination on the large intestine of a patient. The higher the points, the greater the severity.

The "subscore for bloody stool" is given from 0 to 3 points depending on the state of bloody stool of a patient. The higher the points, the greater the severity.

The patients targeted in the present invention are preferably patients at the time when 6 months or more elapse after an ulcerative colitis symptom appears.

In Description and Claims, a patient on whom a 5-ASA preparation has an insufficient effect means a patient on whom a 5-ASA preparation has an insufficient effect even if the 5-ASA preparation is continuously ingested for 4 weeks or more without changing the administration and dosage. Preferably, the patient is a patient on whom an oral 5-ASA preparation has an insufficient effect even if the oral 5-ASA preparation is continuously taken for 4 weeks or more at the clinically adoptable maximum dosage without changing the administration and dosage, and who does not use a combination with an oral corticosteroid preparation in an active stage during which the pharmaceutical composition of the present invention is to be administered. Although varying depending on 5-ASA preparations, the clinically adoptable maximum dosage in Japan is a dosage described below, for example.

Mesalazine preparation (except for Asacol (registered trademark) tablet): 4.0 g/day
Asacol (registered trademark) tablet: 3.6 g/day
Salazosulfapyridine (SASP) preparation: 4 g/day or more Similarly, a patient on whom a corticosteroid preparation has an insufficient effect means a patient on whom a corticosteroid preparation has an insufficient effect even if the corticosteroid preparation is continuously taken for 2 weeks or more without changing the administration and dosage. Preferably, the patient is a patient on whom an oral corticosteroid preparation has an insufficient effect even if the oral corticosteroid preparation is continuously ingested for 2 weeks or more at 30 to 40 mg/day (in terms of prednisolone) without changing the administration and dosage. Moreover, in a case where an oral 5-ASA preparation is used in combination with a corticosteroid preparation, the patient does not change the administration and dosage for 4 weeks or more in addition to the above conditions.

A patient who is intolerant to a 5-ASA preparation means a patient who has difficulty in taking an oral 5-ASA preparation in an amount sufficient for the treatment because the preparation produces or may produce a side effect. Preferably, the patient is a patient who has difficulty in taking an oral 5-ASA preparation in an amount sufficient for the treatment because the preparation produces or may produce a side effect, and who does not change the administration and dosage for 4 weeks or more, so that an oral corticosteroid preparation is not used in combination in an active stage during which the pharmaceutical composition of the present invention is to be administered.

A patient who is intolerant to a corticosteroid preparation means a patient who has difficulty in taking an oral corticosteroid preparation in an amount sufficient for the treatment because the preparation produces or may produce a side effect. Preferably, the patient is a patient who has difficulty in taking an oral corticosteroid preparation in an amount sufficient for the treatment because the preparation produces or may produce a side effect, and who does not change the administration and dosage for 2 weeks or more. Moreover, in a case where an oral 5-ASA preparation is used in combination, the patient is preferably a patient who does not change the administration and dosage for 4 weeks or more in addition to the above conditions.

The pharmaceutical composition of the present invention is preferably administered to a patient who has ulcerative colitis for a period of less than 5 years (more preferably less than 1 year). Moreover, the pharmaceutical composition of the present invention is preferably administered to a patient who has a body weight of 50 kg or more. The pharmaceutical composition of the present invention is more preferably administered to a patient who has a body weight of 50 kg or more and also has ulcerative colitis for a period of less than 5 years (more preferably less than 1 year). Further, the pharmaceutical composition of the present invention may be administered to a patient having ulcerative colitis either occurring for the first time or relapsing, but is preferably administered to a patient having ulcerative colitis relapsing, and preferably administered to a patient who has ulcerative colitis for a period of less than 5 years and also has ulcerative colitis relapsing.

The pharmaceutical composition of the present invention is preferably administered to a patient in an active stage of ulcerative colitis and at the time when 1 month or more elapse after a remission induction therapy of an oral 5-ASA preparation or an oral corticosteroid preparation is started in the active stage. The pharmaceutical composition of the present invention is more preferably administered to a patient 1 month or more but less than 6 months after the remission induction therapy is started, and furthermore preferably administered to a patient 1 month or more but less than 3 months after the remission induction therapy is started.

The pharmaceutical composition of the present invention may be administered to a patient having received a therapy of another oral or parenteral drug for treating ulcerative colitis, or may be administered to a patient having not received the therapy. Nevertheless, the pharmaceutical composition of the present invention is preferably administered to a patient having received the therapy. Above all, the pharmaceutical composition of the present invention is preferably administered to a patient having received a therapy of another parenteral drug for treating ulcerative colitis, more preferably administered to a patient having received a therapy of another enema agent or suppository for treating ulcerative colitis, and furthermore preferably administered to a patient who is in an active stage of ulcerative colitis and also has received a therapy of another enema agent or suppository for treating ulcerative colitis in the active stage. Above all, the pharmaceutical composition of the present invention is preferably administered to a patient who is in an active stage of ulcerative colitis and also has received a therapy of another enema agent or suppository for treating ulcerative colitis in the active stage but terminates the therapy due to an insufficient effect. The pharmaceutical composition of the present invention is particularly preferably administered to a patient who is in an active stage of ulcerative colitis and also has received a therapy of another enema agent or suppository for treating ulcerative colitis in the active stage but terminates the therapy due to an insufficient effect, so that the patient is receiving a drug therapy of an oral 5-ASA preparation and/or an oral corticosteroid preparation. The another enema agent or suppository for treating ulcerative colitis includes an enema agent containing a 5-aminosalicylic acid, a suppository containing a 5-aminosalicylic acid, an enema agent containing a corticosteroid, and a suppository containing a corticosteroid.

The pharmaceutical composition of the present invention may be administered to an ulcerative colitis patient whose most active site of mucosal inflammation is located at an upper portion of the large intestine (sigmoid colon (S), rectosigmoid junction (Rs)) according to an endoscopic evaluation, which is preferably conducted before the administration of the pharmaceutical composition is started. The pharmaceutical composition of the present invention may be administered to an ulcerative colitis patient whose most active site of mucosal inflammation is located at a lower portion of the large intestine (rectum above the peritoneal reflection (Ra), rectum below the peritoneal reflection (Rb)) according to the endoscopic evaluation. Nevertheless, the pharmaceutical composition of the present invention is preferably administered to an ulcerative colitis patient whose most active site of mucosal inflammation is located at an upper portion of the large intestine (S, Rs) according to the endoscopic evaluation. Among these, the pharmaceutical composition of the present invention is particularly preferably administered to an ulcerative colitis patient whose most active site of mucosal inflammation is located at an upper portion of the large intestine (S, Rs) according to the endoscopic evaluation, and who has the disease for a period of less than 5 years.

The pharmaceutical composition of the present invention is preferably administered to an ulcerative colitis patient having a stool frequency of 6 times or less per day preferably in 3 days immediately before the administration of the pharmaceutical composition is started; the pharmaceutical composition of the present invention is more preferably administered to an ulcerative colitis patient who has a stool frequency of 6 times or less per day and also has the disease for a period of less than 5 years, more preferably administered also to an ulcerative colitis patient who has a stool frequency of 6 times or less per day and also has ulcerative colitis relapsing, and furthermore preferably administered to an ulcerative colitis patient who has a stool frequency of 6 times or less per day, the disease for a period of less than 5 years, and also ulcerative colitis relapsing.

<Dosage Per Day>

The compound (1) or the pharmaceutically acceptable salt is administered as an active ingredient in an amount of preferably 600 mg/day or more, more preferably 1500 mg/day or more, and furthermore preferably 2500 mg/day or more, to the target patient. The upper limit is not particularly limited, but is preferably 9000 mg/day or less, more preferably 6000 mg/day, and furthermore preferably 3000 mg/day. Among these, the administration amount is particularly preferably 2500 to 3000 mg/day, and the administration amount is the most preferably 2880 mg/day.

<Number of Times of Administration Per Day>

The number of times of the administration per day is not particularly limited. For example, the compound (1) or the pharmaceutically acceptable salt can be administered 1 to 5 times a day to the target patient. Among these, the compound (1) or the pharmaceutically acceptable salt is preferably administered 1 to 4 times a day, more preferably administered 1 to 3 times a day, and furthermore preferably administered 3 times a day.

Moreover, when the administration is performed multiple times a day, the single dose is preferably an amount obtained by dividing the dosage per day by the number of times of the administration per day.

Among these, the compound (1) or the pharmaceutically acceptable salt is preferably administered 3 times a day at a dose of 200 mg or more per administration, more preferably administered 3 times a day at a dose of 200 to 3000 mg per administration, furthermore preferably administered 3 times a day at a dose of 500 to 2000 mg per administration, furthermore preferably administered 3 times a day at a dose of 800 to 1100 mg per administration, particularly preferably administered 3 times a day at a dose of 900 to 1000 mg per administration, and the most preferably administered 3 times a day at a dose of 960 mg per administration, to the target patient.

<Administration Period>

The administration period is not particularly limited. The administration is possible, for example, until an ulcerative colitis symptom of the target patient is relieved. Above all, the compound (1) or the pharmaceutically acceptable salt is preferably administered for at least 4 weeks, more preferably administered for at least 8 weeks, and furthermore preferably administered for at least 1 year. In addition, the compound (1) or the pharmaceutically acceptable salt is preferably administered for 4 weeks to 8 months, and more preferably administered for 8 weeks to 6 months.

<Dosage Form>

The pharmaceutical composition of the present invention may be an oral preparation, or may be a parenteral preparation (intravenous injection preparation, enema preparation, suppository, or the like). Nevertheless, an oral preparation is preferable. Examples of the oral preparation include tablets, powders, pills, granules, capsules, solution, sugar-coated tablets, depots, syrups, and the like. These can be produced according ordinary methods using ordinary preparation additives.

For example, a tablet is obtained by mixing the compound (1) or the pharmaceutically acceptable salt as the active ingredient of the present invention with a known auxiliary substance, for example, an inactive diluent such as lactose, calcium carbonate, or calcium phosphate; a binder such as gum arabic, corn starch, or gelatin; a bulking agent such as alginic acid, corn starch, or pregelatinized starch; a sweetener such as sucrose, lactose, or saccharin; a flavoring agent such as peppermint, *Gaultheria adenothrix* oil, or cherry; a lubricating and wetting agent such as magnesium stearate, talc, or carboxymethyl cellulose; an excipient for soft gelatin capsule and suppository such as a fat, a wax, semi-solid and liquid polyols, a natural oil, or hydrogenated oil; or an excipient for solution such as water, alcohol, glycerol, polyol, sucrose, invert sugar, glucose, or vegetable oil.

Moreover, the pharmaceutical composition of the present invention may be in a form of solid dispersion in which the compound (1) or the pharmaceutically acceptable salt in an amorphous state is dispersed in a matrix of a water-soluble polymer substance.

The water-soluble polymer substance is not particularly limited, as long as it is water soluble and capable of dissolving or dispersing the compound (1) or the pharmaceutically acceptable salt. Various synthetic polymers and natural polymers are used as the water-soluble polymer substance. These water-soluble polymers preferably include celluloses and derivatives thereof (for example, methyl cellulose, hypromellose (a.k.a.: hydroxypropyl methylcellulose), hydroxypropyl cellulose, hydroxypropyl methylcellulose phthalate, hydroxypropyl methylcellulose acetate succinate, carboxymethylethyl cellulose, sodium carboxymethyl cellulose, hydroxyethyl cellulose, and cellulose acetate phthalate); synthetic polymers (for example, polyethylene glycol, polyvinyl alcohol, polyvinylpyrrolidone, polyvinylacetal diethylaminoacetate, aminoalkyl methacrylate copolymer E, aminoalkyl methacrylate copolymer RS, methacrylic acid copolymer L, methacrylic acid copolymer LD, methacrylic acid copolymer S, and carboxyl vinyl polymer); natural polymers and saccharides (for example, gum arabic, sodium alginate, propylene glycol alginate, agar, gelatin, tragacanth, and xanthan gum); and the like.

Among these, preferable are methyl cellulose, hypromellose, hydroxypropyl cellulose, polyethylene glycol, polyvinyl alcohol, and polyvinylpyrrolidone, and more preferable are methyl cellulose and hypromellose.

These water-soluble polymer substances can be used alone or in combination.

A ratio between the compound of the formula (1) or the pharmaceutically acceptable salt and the water-soluble polymer substance is such that, for example, the latter may be 0.1 to 10 parts by mass, may be 0.5 to 5 parts by mass, or may be 1 to 3 parts by mass, relative to 1 part by mass of the former.

The compound (1) or the pharmaceutically acceptable salt dispersed in the matrix of the water-soluble polymer substance can be prepared, for example, by a solvent method, a melting method, a melt kneading method under heating and pressing, or a mixing and pulverizing method.

Moreover, the pharmaceutical composition of the present invention may comprise crospovidone in addition to the compound of the formula (1) or the pharmaceutically acceptable salt dispersed in the water-soluble polymer substance matrix.

Crospovidone is known as and called 1-ethenyl-2-pyrrolidinon homopolymer and is a crosslinked polymer of 1-vinyl-2-pyrrolidone. The substance is white to light yellowish powder and hardly soluble in water. When crospovidone is used as a disintegrant, the amount is preferably 0.1 to 20% by mass, more preferably 1 to 15% by mass, relative to a total amount of the pharmaceutical composition.

In the pharmaceutical composition of the present invention, crospovidone may be further used in combination with one or two or more disintegrants selected from hydroxypropyl cellulose, low-substituted hydroxypropyl cellulose, croscarmellose sodium, pregelatinized starch (such as partially pregelatinized starch), methyl cellulose, sodium alginate, sodium carboxymethyl starch, carmellose calcium, carmellose sodium, crystalline cellulose, and crystalline cellulose•carmellose sodium. Among these, croscarmellose sodium is preferably used in combination. In this case, croscarmellose sodium is preferably used in combination in an amount of 10 to 1000 parts by mass, more preferably used in combination in an amount of 50 to 600 parts by mass, per 100 parts by mass of crospovidone within an acceptable range of the total amount of the pharmaceutical composition.

The pharmaceutical composition of the present invention may comprise, as necessary, an additive such as an excipient (saccharides (for example, lactose, sucrose, glucose, reduced maltose, mannitol, sorbitol, xylitol, and trehalose), starches and derivatives thereof (for example, pregelatinized starch (such as partially pregelatinized starch), dextrin, pullulan, corn starch, and potato starch), celluloses (for example, crystalline cellulose, microcrystalline cellulose, crystalline cellulose•carmellose sodium, and hydroxypropyl cellulose), magnesium aluminometasilicate, silicon dioxide, light anhydrous silicic acid, amino acids, and the like), a coloring agent, a corrigent (for example, sucrose, aspartame, mannitol, dextran, saccharin, menthol, citric acid, tartaric acid, malic acid, ascorbic acid, amacha, fennel, ethanol, fructose, xylitol, glycyrrhizic acid, purified sucrose, L-glutamic acid, and cyclodextrin), a lubricant (for example, magnesium stearate, talc, light anhydrous silicic acid, calcium stearate, magnesium oxide, magnesium lauryl sulfate, and magnesium aluminometasilicate), and a surfactant (for example, sodium lauryl sulfate, polysorbate 80, sucrose fatty acid esters, polyoxyl 40 stearate, polyoxyethylene hardened castor oil 60, sorbitan monostearate, and sorbitan monopalmitate). Further, a foaming agent (for example, sodium hydrogen carbonate and ammonium carbonate) and the like may be incorporated.

As the excipient, at least one selected from mannitol, pregelatinized starch (such as partially pregelatinized starch), and crystalline cellulose is preferably incorporated.

Moreover, a coated tablet of the pharmaceutical composition of the present invention may be prepared by obtaining a tablet and then providing a coating agent on the surface of the tablet.

Any coating agent can be used, as long as it is commonly used in the pharmaceutical industries. Examples thereof include acrylic acid derivatives (for example, methacrylic acid copolymer L, methacrylic acid copolymer S, methacrylic acid copolymer LD, and aminoalkyl methacrylate copolymer E), cellulose derivatives (for example, hydroxypropyl methylcellulose phthalate, hydroxypropyl methylcellulose acetate succinate, carboxymethylethyl cellulose, cellulose acetate phthalate, hydroxyethyl cellulose, hydroxypropyl cellulose, hypromellose, methyl cellulose, methyl hydroxyethyl cellulose, Opadry, carmellose calcium, and carmellose sodium), vinyl derivatives (for example, polyvinylpyrrolidone, polyvinyl alcohol, and polyvinylacetal diethylaminoacetate), starches (dextrin and pullulan), and natural polymers and saccharides (for example, shellac, gelatin, agar, and gum arabic). One or two or more of these coating agents can be used.

Among these, water-soluble polymers are preferable; aminoalkyl methacrylate copolymer E, hypromellose, methyl cellulose, methyl hydroxyethyl cellulose, Opadry, carmellose calcium, carmellose sodium, polyvinylpyrrolidone, polyvinyl alcohol, dextrin, pullulan, gelatin, agar, and gum Arabic are preferable.

In the event of coating, in order to help the film formability of a film substrate and to provide an additional characteristic, for example, a plasticizer (for example, polyethylene glycol, sucrose fatty acid esters, glycerin fatty acid esters, propylene glycol, triethyl citrate, castor oil, or triacetin), or a light shielding agent (for example, titanium oxide or ferric oxide) can also be used in combination.

The amount of the coating can be adjusted, so that, for example, the percentage of the solid content covering the preparation is 0.1 to 20% by mass, 0.5 to 10% by mass, or 1 to 7% by mass.

<Concomitant Agent>

The pharmaceutical composition of the present invention can also be used in combination with another drug having therapeutic and/or prophylactic effects against ulcerative colitis.

The another drug having therapeutic and/or prophylactic effects against ulcerative colitis includes elemental diets or component nutrition agents (such as Elental (registered trademark) (Ajinomoto Co., Inc.)), 5-ASA preparations (such as mesalazine and salazosulfapyridine (sulfasalazine)), corticosteroid preparations (such as prednisolone, betamethasone, and budesonide), and antibiotics agents (such as metronidazole).

Moreover, the drug used in combination also includes immunosuppressants (such as azathioprine, 6-mercaptopurine, cyclosporin, and tacrolimus).

Further, anti-cytokine agents also include anti-TNFα antibodies (such as infliximab, adalimumab, certolizumabpegol, and golimumab), anti-IL-6 receptor antibodies (such as tocilizumab), anti-IL-12/23 antibodies (such as ustekinumab and briakinumab), anti-IL-17 receptor antibodies (such as AMG827 and AIN457), IL-12/23 production inhibitors (such as STA-5326) as low-molecular-weight agents, PDE-4 inhibitors (such as tetomilast), chemokine inhibitors (such as vercirnon and CCX507), Janus kinase inhibitors (such as tofacitinib and GLPG0634), SIP agonists (such as KRP203 and RPC1063).

Alternatively, without limitation to the drugs, another therapeutic method having therapeutic and/or prophylactic effects against the disease can also be used in combination. Examples thereof include leukocyte apheresis (such as GCAP and LCAP).

From the foregoing, the pharmaceutical composition of the present invention can be used in combination with another drug having therapeutic and/or prophylactic effects against the disease. In addition, the pharmaceutical composition of the present invention can also be used in combination with another therapeutic method against the disease.

When used in combination with another drug, the pharmaceutical composition of the present invention and the another drug may be administered simultaneously, may be administered sequentially, or may be administered separately at certain time intervals.

The dosage form of the drug to be used in combination is not particularly limited and includes oral preparations, injections, enema preparations, suppositories, and the like. Nevertheless, for a patient having a lesion around the anus and other similar patients, an enema agent or a suppository is preferably used in combination.

Examples

Hereinafter, the present invention will be described specifically based on Examples. However, the present invention is not limited to the contents descried therein.

<Subjects>

Subjects were ulcerative colitis patients in an active stage who satisfied the following conditions.

(1) Moderately active ulcerative colitis patient having a Mayo score of 6 points or more but 10 points or less on the eligibility verification day (2) Patient having a Mayo score with a "subscore for mucosal finding" of 2 points or more and a "subscore for bloody stool" of 1 point or more on the eligibility verification day (3) Patient on whom a drug therapy of an oral 5-ASA preparation (including a salazosulfapyridine (SASP) preparation) or an oral corticosteroid preparation has an insufficient effect or who is intolerant to even the drug therapy (4) Patient at the time when 6 months or more had elapsed, on the eligibility verification day, after an ulcerative colitis symptom appeared (5) Patient who was 20 years old or older but less than 65 years when the consent was provided (6) Patient receiving an ambulatory therapy (7) Patient who was able to provide a written consent <Drug Preparation in Example 1 or Comparative Example 1>

A tablet comprising 120 mg of the compound of the formula (1) was coated with a film. Thus, a film-coated tablet was prepared (compound of Example 1).

Moreover, a tablet comprising no compound of the formula (1) was coated with a film. Thus, a film-coated tablet was prepared (compound (placebo) of Comparative Example 1) which was difficult to distinguish from the compound of Example 1 by the external appearance (shape, color, and so forth).

<Administration>

The compound of Example 1 or the compound of Comparative Example 1 was orally administered after meals 3 times a day. The number of the given tablets was 8 per administration (i.e., the amount of the compound (1) of Example 1 administered was 960 mg per administration). The administration period was 8 weeks. The compounds were administered until the timing after the breakfast on the day before the assessment day at Week 8.

As the subjects, 102 cases (Comparative Example 1: 51 cases, Example 1: 51 cases) were analyzed for assessment items to be described later.

Note that the use of and the treatment with the following drugs were prohibited until the final observation and examination after the drug administration was started.

5-ASA preparation (enema agent)
SASP preparation (suppository)
Corticosteroid preparations (injection, intravenous injection, intraarterial injection, enema agent, suppository, any agent for treating hemorrhoidal disease)
Apheresis
Immunomodulating agents (azathioprine, 6-mercaptopurine, cyclosporin, tacrolimus, methotrexate, and the like)
Nevertheless, the use of external agents was not prohibited.
Anti-TNF-α antibody preparations
Antibiotics and antimicrobial agents for treating ulcerative colitis
Blood transfusion
Anti-diarrheal drugs
Agents for treating diarrhea-predominant irritable bowel syndrome
Surgical therapy against ulcerative colitis
Whole bowel irrigation agents (except for the use in the pre-treatment of the endoscopic examination on the large intestine for this clinical study)
Laxatives (except for the use in the pre-treatment of the endoscopic examination on the large intestine for this clinical study)
Enemas (except for the use in the pre-treatment of the endoscopic examination on the large intestine for this clinical study)
The use of the other study drugs or participation in the other clinical studies Note that when the provision of prohibiting concomitant drugs and treatments was not fulfilled because the therapeutic method had to be changed due to a worsening or the like of ulcerative colitis during the clinical study, the participation in the clinical study was discontinued. Then, necessary observation and examination were conducted in the event of the discontinuation.

Other concomitant drugs (treatments) than those prohibited above were allowed to be used in combination. Nevertheless, the administration and dosage of the following drugs, if having been continuously administered prior to the eligibility verification day, were not changed from the eligibility verification day until the final observation and examination (in the cases of discontinuation, the observation and examination were conducted on the items in the event of the discontinuation).

(1) Oral 5-ASA preparations (including a SASP preparation)
(2) Oral corticosteroid preparations (*)
(3) Antiflatulent drugs
(*) A gradual reduction by "5 mg or less every 2 weeks" was allowed at and from Week 2 after the study drug administration was started.

Note that the change in the administration and dosage of drugs was prohibited if the change in the administration and dosage conceivably influenced the efficacy assessment of the present drug. Nonetheless, regarding the corticosteroid preparations, it was believed that the continuous administration with the same administration and dosage as those at the time of the eligibility verification for 2 weeks prior to the eligibility verification day and for further 8 weeks of the administration period of the study drug was ethically a problem for patients who showed an improvement in the disease state. For this reason, the dosage reductions were allowed under such a condition as to reduce the influence on the efficacy assessment of the present drug as much as possible in accordance with the treatment guideline against ulcerative colitis revised in 2010.

<Mayo Score>

The investigators or sub-investigators assessed subscores ("stool frequency," "bloody stool," "mucosal finding," and "physician's global assessment") of the Mayo score according to (1) to (4) below. A Mayo score was a total value of four subscore items of "stool frequency," "bloody stool," "mucosal finding," and "physician's global assessment." Meanwhile, a partial Mayo score was a total value of three subscore items of the Mayo score excluding "mucosal finding." Note that, for the Mayo score and the partial Mayo score at Week 0, scores obtained at the time of the eligibility determination were used.

<Subscores of Mayo Score>

(1) Stool Frequency
[Investigation Timings: Weeks 0, 2, 4, and 8 (or Discontinuation Time)]

Investigation of Stool Frequency

Based on the contents described in the symptom-recording diaries and so on, the investigators or sub-investigators investigated stool frequencies in 3 days immediately before each assessment day. Note that when the endoscopic examination on the large intestine was conducted, the investigation days were set to be the closest three days excluding the day of the endoscopic examination on the large intestine, the following day, and if a pre-treatment was performed for the endoscopic examination on the large intestine, the pre-treatment day.

Scoring Stool Frequency

The investigators or sub-investigators investigated the stool frequency per day before the primary disease appeared, which served as a "normal frequency." An average value (rounded to the nearest whole number) of the stool frequencies of the investigated three days was compared with the "normal frequency," and scored according to the following criteria.

| Score | Stool frequency |
|---|---|
| 0 | Normal frequency |
| 1 | 1 to 2 times more than normal frequency per day |
| 2 | 3 to 4 times more than normal frequency per day |
| 3 | At least 5 times more than normal frequency per day |

(2) Bloody Stool
[Investigation Timings: Weeks 0, 2, 4, and 8 (or Discontinuation Time)]

Investigation of Bloody Stool

Based on the contents described in the symptom-recording diaries, the investigators or sub-investigators investigated the states of bloody stool in 3 days immediately before each assessment day. Note that when the endoscopic examination on the large intestine was conducted, the investigation days were set to be the closest three days excluding the day of the endoscopic examination on the large intestine, the following day, and if a pre-treatment was performed for the endoscopic examination on the large intestine, the pre-treatment day.

Scoring Bloody Stool

The bloody stool state on the most severe day among the investigated three days was scored according to the following criteria.

| Score | Bloody stool |
|---|---|
| 0 | No bloody stool |
| 1 | Blood was slightly spotted (streaks) at most half stooling occasions |
| 2 | Obvious blood inclusion was observed in most of stooling occasions |
| 3 | Mostly blood |

(3) Mucosal Finding (Large Intestine Endoscopic Examination)
[Investigation Timings: Weeks 0 and 8 (or Discontinuation Time)]

Conducting Large Intestine Endoscopic Examination

The investigators or sub-investigators conducted the endoscopic examination on the large intestine, and checked the state of the large intestinal mucosa.

(a) Week 0

The assessment result used in the eligibility verification was used as the assessment result at Week 0.

(b) Week 8

The endoscopic examination was conducted during a time from 7 days before Week 8 (or discontinuation time) until a medical interview at Week 8 (or discontinuation time). Note that the endoscopic examination on the large intestine at Week 8 (or discontinuation time) was conducted by the same physician at Week 0 when the situation allowed.

Scoring Mucosal Finding

When the endoscopic examination on the large intestine was conducted, the investigators or sub-investigators assessed the most active site, and scored the mucosal finding according to the following criteria.

At Week 0, the most active site was specified. The assessment at the site served as the "subscore for mucosal finding" of the Mayo score. At Week 8 (or discontinuation time) also, the same site as that at Week 0 was assessed as the "subscore for mucosal finding" of the Mayo score.

| Score | Mucosal finding (up to sigmoid colon) |
|---|---|
| 0 | Normal or inactive finding |
| 1 | Mild (erythema, decrease in vascular pattern, mild weakening) |
| 2 | Moderate (remarkable erythema, loss of vascular pattern, weakening, erosions) |
| 3 | Severe (natural bleeding, ulcers) |

(4) Physician's Global Assessment
[Investigation Timings: Weeks 0, 2, 4, and 8 (or Discontinuation Time)]

Conducting Medical Interview

The investigators or sub-investigators conducted a medical interview with the subjects (for abdominal discomfort, systemic state, investigator's finding, subject's impression, and so forth), and investigated the state on each assessment day.

Scoring Physician's Global Assessment

The investigators or sub-investigators scored the physician's global assessment according to the following criteria with reference to the other three assessment criteria (stool frequency, bloody stool, and mucosal finding), as well as the abdominal discomfort, systemic state, investigator's finding, subject's impression, and so forth. Note that, on the days of the assessment performed without an endoscope, no mucosal finding was considered in scoring the physician's global assessment.

| Score | Physician's global assessment |
|---|---|
| 0 | Normal |
| 1 | Mild |
| 2 | Moderate |
| 3 | Severe |

<<Study Results>>

First, the response rates were assessed.

<Response Rate>

A proportion of subjects satisfying the following conditions (a) and (b) (response rate):

(a) the Mayo score was reduced by 30% or more and by 3 points or more in comparison with that at Week 0; and
(b) the subscore for bloody stool was reduced by 1 point or more in comparison with that at Week 0 or was 1 point or less.

Regarding the response rate (proportion of response cases) (Week 8), Example 1 was compared with Comparative Example 1 by setting a logistic regression model using the following adjusting factors as covariates to conduct a superiority test.

Adjusting Factors:

1. either subjects on whom a 5-ASA preparation (including a SASP preparation) or a corticosteroid preparation has an insufficient effect or who are intolerant to a 5-ASA preparation (including a SASP preparation) or a corticosteroid preparation; and
2. the Mayo scores (6 points or more but 7 points or less, 8 points or more but 10 points or less) on the eligibility verification day.

(1) Main Analysis

Using the response rate at Week 8 as a primary endpoint, a main effect model was set as the main analysis. As a result of analyzing the logistic regression model using the response rate (Week 8) as a target variable, and using the administration group and the adjusting factors (either subjects on whom a 5-ASA preparation (including a SASP preparation) or a corticosteroid preparation has an insufficient effect or who are intolerant to a 5-ASA preparation (including a SASP preparation) or a corticosteroid preparation and the Mayo scores on the eligibility verification day) as explanatory variables, the p-value of Wald$\chi^2$ of the administration group was significant with p=0.0002. An estimate of an odds ratio of Example 1 to Comparative Example 1 (placebo group) was 5.35, and the two-sided 95% confidence interval was 2.23 to 12.82. Note that, in an interaction effect model, the interaction term was not significant.
(2) Subanalysis
(i) Estimation of Difference Between Groups without Using Model with Primary Endpoint Table 5 shows the response rates and an estimation of a difference in the response rates, and FIG. 1 shows the response rates.

The response rate was 25.5% (13/51 cases) in Comparative Example 1 (placebo group), while that in Example 1 was 62.7% (32/51 cases). The difference between the two groups was 37.3%, and the two-sided 95% confidence interval was 18.1% to 52.8%.

|  | Number of cases analyzed | Response cases | Response rate (%) | 95% confidence interval | Comparison of Example 1 with Comparative Example 1 | |
|---|---|---|---|---|---|---|
| Administration group |  |  |  |  | Difference in response rates | 95% confidence interval of difference |
| Comparative Example 1 | 51 | 13 | 25.5 | 15.5 to 38.9 | — | — |
| Example 1 | 51 | 32 | 62.7 | 49.0 to 74.7 | 37.3 | 18.1 to 52.8 |

(ii) Subgroup Analyses

Regarding the adjusting factor of either subjects on whom a 5-ASA preparation (including a SASP preparation) or a corticosteroid preparation has an insufficient effect or who are intolerant to a 5-ASA preparation (including a SASP preparation) or a corticosteroid preparation, the response rate of the subjects on whom a 5-ASA preparation (including a SASP preparation) had an insufficient effect was 23.9% (11/46 cases) in the administration group of Comparative Example 1, while that in the administration group of Example 1 was 60.9% (28/46 cases). The response rate of the subject being intolerant to a 5-ASA preparation (including a SASP preparation) was 100.0% (1/1 case) in Comparative Example 1 (placebo group), while that in Example 1 was 100.0% (2/2 cases). The response rate of the subject on whom a corticosteroid preparation had an insufficient effect was 0.0% (0/1 case) in Comparative Example 1 (placebo group), while that in Example 1 was 100.0% (2/2 cases). The response rate of the subjects being intolerant to a corticosteroid preparation was 33.3% (1/3 cases) in Comparative Example 1 (placebo group), while that in Example 1 was 0.0% (0/1 case).

Likewise, regarding the adjusting factor of the Mayo scores (6 points or more but 7 points or less, 8 points or more but 10 points or less) on the eligibility verification day, the response rate of the subjects each having the Mayo score (6 points or more but 7 points or less) was 31.8% (7/22 cases) in Comparative Example 1 (placebo group), while that in Example 1 was 75.0% (15/20 cases). The response rate of the subjects each having the Mayo score (8 points or more but 10 points or less) was 20.7% (6/29 cases) in Comparative Example 1 (placebo group), while that in Example 1 was 54.8% (17/31 cases).

Regarding the gender, the response rate of the males was 23.1% (6/26 cases) in Comparative Example 1 (placebo group), while that in Example 1 was 61.3% (19/31 cases). The response rate of the females was 28.0% (7/25 cases) in Comparative Example (placebo group), while that in Example 1 was 65.0% (13/20 cases).

Regarding the disease period (year), the response rate of the subjects having the disease for less than 1 year was 25.0% (1/4 cases) in Comparative Example 1 (placebo group), while that in Example 1 was 100.0% (6/6 cases). The response rate of the subjects having the disease for 1 year or more but less than 5 years was 20.0% (3/15 cases) in Comparative Example 1 (placebo group), while that in Example 1 was 61.9% (13/21 cases). The response rate of the subjects having the disease for 5 years or more was 28.1% (9/32 cases) in Comparative Example 1 (placebo group), while that in Example 1 was 54.2% (13/24 cases).

Regarding the categories according to the site affected with the primary disease, the response rate of the pancolitis subjects was 20.0% (4/20 cases) in Comparative Example 1 (placebo group), while that in Example 1 was 59.1% (13/22 cases). The response rate of the left-sided colitis subjects was 29.0% (9/31 cases) in Comparative Example 1 (placebo group), while that in Example 1 was 65.5% (19/29 cases).

As a result of the above-described subgroup analyses such as the gender, the disease period, and the categories according to the site affected with the primary disease, the response rate of the administration group of Example 1 was higher than that of Comparative Example 1 (placebo group).

Regarding the categories according to the primary disease occurring for the first time and relapsing, the response rate of the subjects having the disease occurring for the first time was 0% (0/3 cases) in Comparative Example 1 (placebo group), while that in Example 1 was 60.0% (3/5 cases). The response rate of the subjects having the disease relapsing was 27.1% (13/48 cases) in Comparative Example 1 (placebo group), while that in Example 1 was 63.0% (29/46 cases).

Among the relapsing subjects, the response rate of the subjects whose disease periods were less than 5 years was 25.0% (4/16 cases) in Comparative Example 1 (placebo group), while that in Example 1 was 72.7% (16/22 cases).

Regarding the period (month) after the remission induction therapy was started with an oral 5-ASA preparation or an oral corticosteroid preparation in the active stage this time, the response rate of the subjects whose periods were less than 1 month was 41.7% (5/12 cases) in Comparative Example 1 (placebo group), while that in Example 1 was 61.5% (8/13 cases). The response rate of the subjects whose periods were 1 month or more but less than 3 months was 16.7° (3/18 cases) in Comparative Example 1 (placebo group), while that in Example 1 was 76.5° (13/17 cases). The response rate of the subjects whose periods were 3 months or more but less than 6 months was 27.3° (3/11 cases) in Comparative Example 1 (placebo group), while that in Example 1 was 60.0% (6/10 cases). The response rate of the subjects whose periods were 6 months or more was 20.0% (2/10 cases) in Comparative Example 1 (placebo group), while that in Example 1 was 45.5% (5/11 cases).

Regarding the categories according to the therapy in the active stage this time, the response rate of the subjects not receiving a therapy of an enema agent or suppository (5-ASA preparation or corticosteroid preparation) in the active stage this time was 31.6% (12/38 cases) in Comparative Example 1 (placebo group), while that in Example 1 was 61.8% (21/34 cases), the responserate of the subjects having received the therapy of an enema agent or suppository (5-ASA preparation or corticosteroid preparation) in the active stage this time but terminated the therapy due to an insufficient effect was 7.7% (1/13 cases) in Comparative Example 1 (placebo group), while that in Example 1 was 64.7% (11/17 cases).

Regarding the categories according to the body weight, the response rate of the subjects of less than 50 kg was 44.4% (4/9 cases) in Comparative Example 1 (placebo group), while that in Example 1 was 55.6% (5/9 cases). The response rate of the subjects of 50 kg or more but less than 60 kg was 16.7% (3/18 cases) in Comparative Example 1 (placebo group), while that in Example 1 was 69.2% (9/13 cases). The response rate of the subjects of 60 kg or more but less than 70 kg was 18.2% (2/11 cases) in Comparative Example 1 (placebo group), while that in Example 1 was 55.6° (10/18 cases). The response rate of the subjects of 70 kg or more was 30.8% (4/13 cases) in Comparative Example 1 (placebo group), while that in Example 1 was 72.7° (8/11 cases).

The response rate of the subjects having body weights of 50 kg or more and also the disease periods of less than 5 years was 13.3% (2/15 cases) in Comparative Example 1 (placebo group), while that in Example 1 was 72.7% (16/22 cases). The remission rate of these subjects was 0% (0/15 cases) in Comparative Example 1 (placebo group), while that in Example 1 was 31.8% (7/22 cases). The mucosal remission rate of these subjects was 26.7% (4/15 cases) in Comparative Example 1 (placebo group), while that in Example 1 was 72.7% (16/22 cases).

Regarding the categories according to the endoscopic evaluation site (the most active site of mucosal inflammation) before the present drug administration was started, the response rate of the subjects whose most active sites of mucosal inflammation were located at Ra or Rb was 23.3% (7/30 cases) in Comparative Example 1 (placebo group), while that in Example 1 was 53.6% (15/28 cases). The response rate of the subjects whose most active sites of mucosal inflammation were located at S or Rs was 28.6% (6/21 cases) in Comparative Example 1 (placebo group), while that in Example 1 was 73.9% (17/23 cases).

The response rate of the subjects whose most active sites of mucosal inflammation before the present drug administration was started were located at S or Rs and also disease periods were less than 5 years was 20.0% (2/10 cases) in Comparative Example 1 (placebo group), while that in Example 1 was 90.0% (9/10 cases).

Regarding the categories according to the stool frequency per day in 3 days immediately before the present drug administration was started, the response rate of the subjects of 6 times or less was 28.9% (11/38 cases) in Comparative Example (placebo group), while that in Example 1 was 75.7% (28/37 cases). The response rate of the subjects of 7 times or more was 15.4% (2/13 cases) in Comparative Example 1 (placebo group), while that in Example 1 was 28.6% (4/14 cases).

The response rate of the subjects who had stool frequencies of 6 times or less per day in 3 days immediately before the present drug administration was started and also the disease periods were less than 5 years was 28.6% (4/14 cases) in Comparative Example 1 (placebo group), while that in Example 1 was 80.0% (16/20 cases).

The response rate of the relapsing subjects who had stool frequencies of 6 times or less per day in 3 days immediately before the present drug administration was started was 30.6% (11/36 cases) in Comparative Example 1 (placebo group), while that in Example 1 was 78.1% (25/32 cases).

Next, the following items (1) to (10) were assessed.

(1) Remission Rate

A remission rate is a proportion of subjects each having a Mayo score of 2 points or less with the individual subscores of 1 point or less.

Table 6 shows the remission rates and an estimation of a difference in the remission rates, and FIG. 2 shows the remission rates.

| Administration group | Number of cases analyzed | Remission cases | Remission rate (%) | 95% confidence interval | Comparison of Example 1 with Comparative Example 1 | |
|---|---|---|---|---|---|---|
| | | | | | Difference in remission rates | 95% confidence interval of difference |
| Comparative Example 1 | 51 | 2 | 3.9 | 1.1 to 13.2 | — | — |
| Example 1 | 51 | 12 | 23.5 | 14.0 to 36.8 | 19.6 | 6.3 to 33.1 |

The remission rate was 3.9% (2/51 cases) in Comparative Example 1 (placebo group), while that in Example 1 was 23.5% (12/51 cases). The difference between the two groups was 19.6%, and the two-sided 95% confidence interval was 6.3% to 33.1%.

(2) Changes in Mayo Scores

Table 7 shows descriptive statistics of the Mayo scores, and FIG. 3 shows changes over time in the Mayo scores.

| | Administration group | Comparative Example 1 | Example 1 |
|---|---|---|---|
| Week 0 | Number of cases | 51 | 51 |
| | Mean | 7.7 | 7.8 |
| | Standard deviation | 1.2 | 1.2 |
| | Maximum | 10 | 10 |
| | Upper quartile | 9.0 | 9.0 |
| | Median | 8.0 | 8.0 |
| | Lower quartile | 7.0 | 7.0 |
| | Minimum | 6 | 6 |
| | Lower 95% confidence interval | 7.4 | 7.5 |
| | Upper 95% confidence interval | 8.1 | 8.1 |
| Week 8 | Number of cases | 44 | 47 |
| | Mean | 6.1 | 4.0 |
| | Standard deviation | 2.4 | 2.4 |
| | Maximum | 12 | 9 |
| | Upper quartile | 8.0 | 5.0 |
| | Median | 6.0 | 4.0 |
| | Lower quartile | 4.0 | 2.0 |
| | Minimum | 0 | 0 |

-continued

| | | |
|---|---|---|
| Lower 95% confidence interval | 5.4 | 3.3 |
| Upper 95% confidence interval | 6.9 | 4.7 |

Difference in mean between Example 1 and Comparative Example 1, and 95% confidence interval

| Assessment timing | Mean | 95% confidence interval |
|---|---|---|
| week 8 | −2.14 | −3.15 to −1.13 |

The Mayo scores were 7.7±1.2 (mean±standard deviation) at Week 0 and 6.1±2.4 at Week 8 in Comparative Example 1 (placebo group), while those in Example 1 were 7.8±1.2 at Week 0 and 4.0±2.4 at Week 8. The difference in the mean between the groups at Week 8 was −2.14, and the two-sided 95% confidence interval was −3.15 to −1.13.

(3) Mucosal Remission Rate

A mucosal remission rate is a proportion of subjects each having a Mayo score with a subscore for mucosal finding of 1 point or less.

Figure 4:
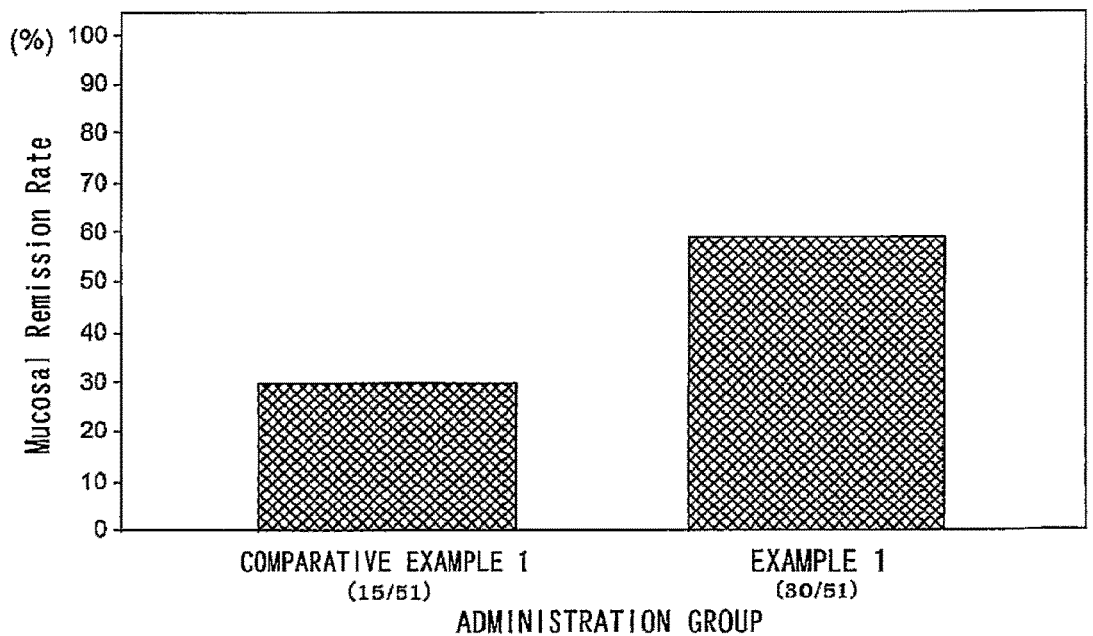
FIG. 4 is a graph showing mucosal remission rates of the administration groups in Example 1 and Comparative Example 1.

Table 8 shows the mucosal remission rates and an estimation of a difference in the mucosal remission rates, and FIG. 4 shows the mucosal remission rates.

| Administration group | Number of cases analyzed | Mucosal remission cases | Mucosal remission rate (%) | 95% confidence interval | Comparison of Example 1 with Comparative Example 1 | |
|---|---|---|---|---|---|---|
| | | | | | Difference in mucosal remission rates | 95% confidence interval of difference |
| Comparative Example 1 | 51 | 15 | 29.4 | 18.7 to 43.0 | — | — |
| Example 1 | 51 | 30 | 58.8 | 45.2 to 71.2 | 29.4 | 10.1 to 45.8 |

The mucosal remission rate was 29.4% (15/51 cases) in Comparative Example 1 (placebo group), while that in Example 1 was 58.8% (30/51 cases). The difference between the two groups was 29.4%, and the two-sided 95% confidence interval was 10.1% to 45.8%.

(4) Changes in Subscores for Mucosal Finding of Mayo Scores

Figure 5:
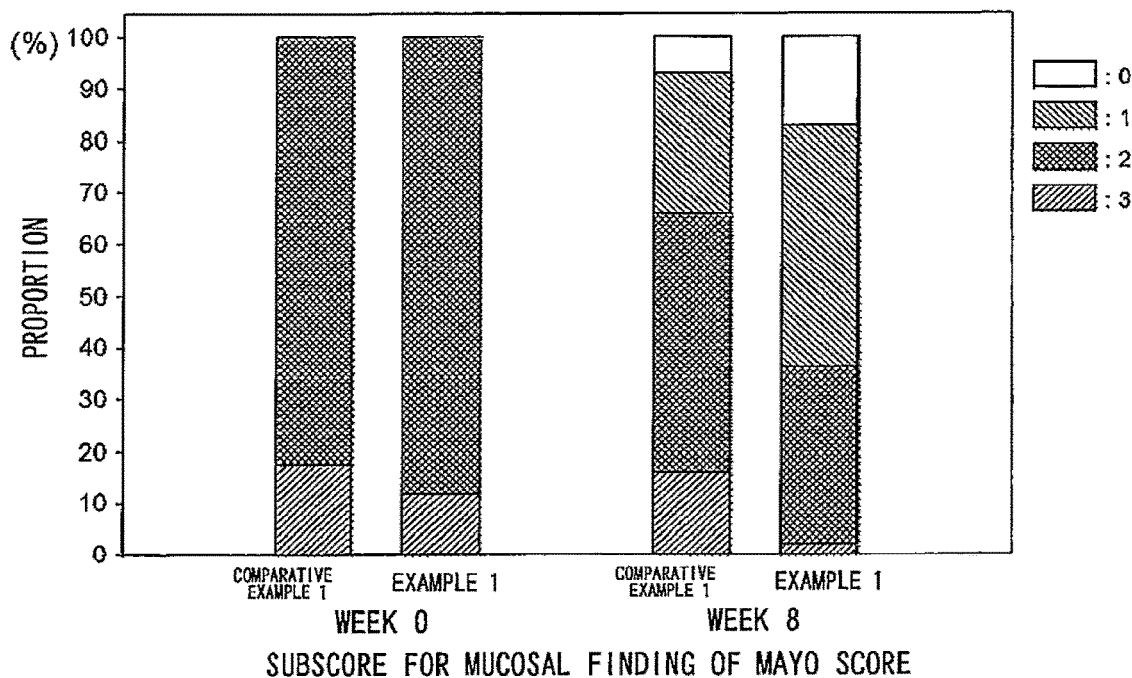
FIG. 5 is a graph showing changes in subscores for mucosal finding of the administration groups in Example 1 and Comparative Example 1.

Table 9 shows a cross tabulation of the subscores for mucosal finding of the Mayo scores, and FIG. 5 shows changes therein.

| Assessment time | Administration group | Number of cases analyzed | Score | | | |
|---|---|---|---|---|---|---|
| | | | 0 | 1 | 2 | 3 |
| Week 0 | Comparative Example 1 | 51 | — | — | 42 (82.4) | 9 (17.6) |
| | Example 1 | 51 | — | — | 45 (88.2) | 6 (11.8) |
| Week 8 | Comparative Example 1 | 44 | 3 (6.8) | 12 (27.3) | 22 (50.0) | 7 (15.9) |
| | Example 1 | 47 | 8 (17.0) | 22 (46.8) | 16 (34.0) | 1 (2.1) |

| Administration group | Assessment time | | Week 0 | |
|---|---|---|---|---|
| | | | 2 | 3 |
| Comparative Example 1 | Week 8 | 0 | 3 | 0 |
| | | 1 | 12 | 0 |
| | | 2 | 20 | 2 |
| | | 3 | 1 | 6 |
| Example 1 | Week 8 | 0 | 7 | 1 |
| | | 1 | 22 | 0 |
| | | 2 | 13 | 3 |
| | | 3 | 0 | 1 |

(5) Partial Mayo Score

Figure 6:
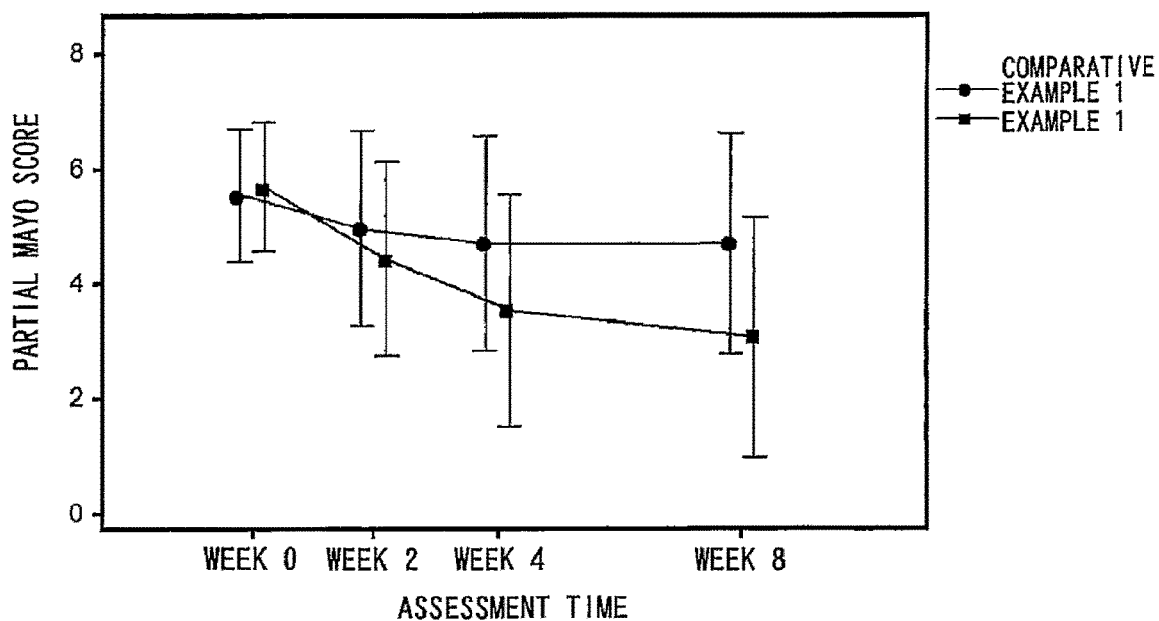
FIG. 6 is a graph showing changes over time in partial Mayo scores of the administration groups in Example 1 and Comparative Example 1.

Table 10 shows descriptive statistics of the partial Mayo scores, and FIG. 6 shows changes over time therein.

| | Administration group | Comparative Example 1 | Example 1 |
|---|---|---|---|
| Week 0 | Number of cases | 51 | 51 |
| | Mean | 5.5 | 5.7 |
| | Standard deviation | 1.2 | 1.1 |
| | Maximum | 8 | 8 |
| | Upper quartile | 6.0 | 6.0 |
| | Median | 6.0 | 6.0 |
| | Lower quartile | 5.0 | 5.0 |
| | Minimum | 4 | 4 |
| | Lower 95% confidence interval | 5.2 | 5.4 |
| | Upper 95% confidence interval | 5.9 | 6.0 |
| Week 2 | Number of cases | 51 | 51 |
| | Mean | 5.0 | 4.4 |
| | Standard deviation | 1.7 | 1.7 |
| | Maximum | 9 | 8 |
| | Upper quartile | 6.0 | 6.0 |
| | Median | 5.0 | 5.0 |
| | Lower quartile | 4.0 | 3.0 |
| | Minimum | 1 | 0 |
| | Lower 95% confidence interval | 4.5 | 4.0 |
| | Upper 95% confidence interval | 5.5 | 4.9 |
| Week 4 | Number of cases | 51 | 51 |
| | Mean | 4.7 | 3.5 |
| | Standard deviation | 1.9 | 2.0 |
| | Maximum | 9 | 8 |
| | Upper quartile | 6.0 | 5.0 |
| | Median | 5.0 | 3.0 |
| | Lower quartile | 3.0 | 2.0 |
| | Minimum | 0 | 0 |
| | Lower 95% confidence interval | 4.2 | 3.0 |
| | Upper 95% confidence interval | 5.2 | 4.1 |
| Week 8 | Number of cases | 51 | 51 |
| | Mean | 4.7 | 3.1 |
| | Standard deviation | 1.9 | 2.1 |
| | Maximum | 9 | 8 |
| | Upper quartile | 6.0 | 4.0 |
| | Median | 5.0 | 3.0 |
| | Lower quartile | 3.0 | 2.0 |
| | Minimum | 0 | 0 |
| | Lower 95% confidence interval | 4.2 | 2.5 |
| | Upper 95% confidence interval | 5.2 | 3.7 |

| Difference in mean between Example 1 and Comparative Example 1, and 95% confidence interval | | |
|---|---|---|
| Assessment timing | Mean | 95% confidence interval |
| Week 2 | −0.55 | −1.22 to 0.12 |
| Week 4 | −1.16 | −1.92 to −0.39 |
| week 8 | −1.63 | −2.42 to −0.84 |

The partial Mayo scores were 5.5±1.2 (mean±standard deviation) at Week 0, 5.0±1.7 at Week 2, 4.7±1.9 at Week 4, and 4.7±1.9 at Week 8 in Comparative Example 1 (placebo group), while those in Example 1 were 5.7±1.1 at Week 0, 4.4±1.7 at Week 2, 3.5±2.0 at Week 4, and 3.1±2.1 at Week 8. The differences in the mean between the groups were −0.55 at Week 2 (the two-sided 95% confidence interval was −1.22 to 0.12), −1.16 at Week 4 (the two-sided 95% confidence interval was −1.92 to −0.39), and −1.63 at Week 8 (the two-sided 95% confidence interval was −2.42 to −0.84).

(6) Changes in Subscores for Stool Frequency of Mayo Scores

Figure 7:
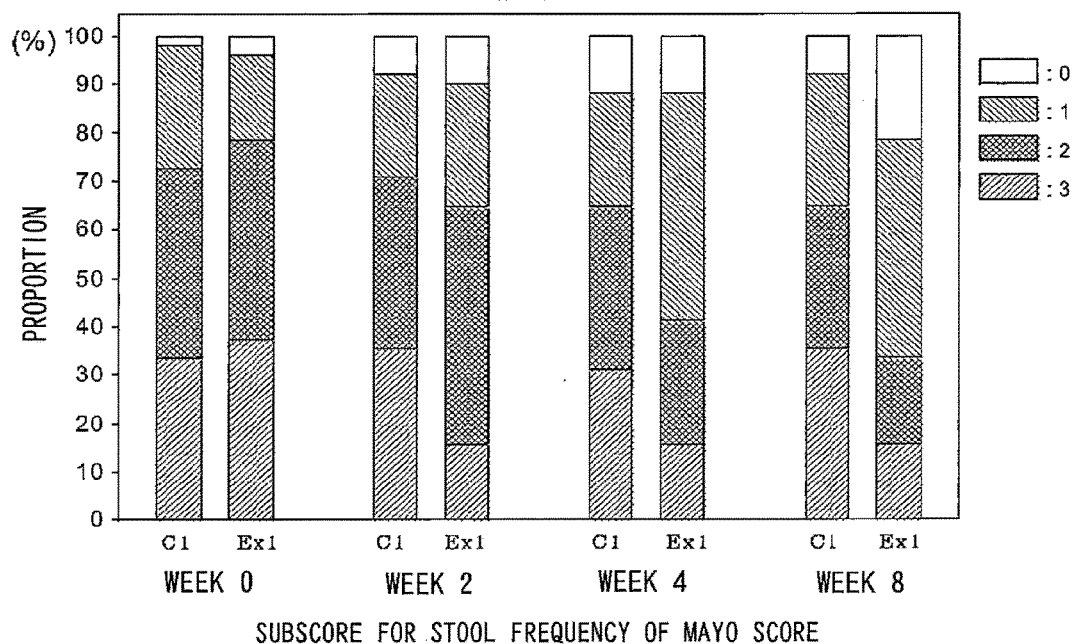
FIG. 7 is a graph showing changes in subscores for stool frequency of the administration groups in Example 1 and Comparative Example 1.

Table 11 shows a cross tabulation of the subscores for stool frequency of the Mayo scores, and FIG. 7 shows changes therein. Note that, in FIG. 7, C1 means Comparative Example 1, and Ex1 means Example 1.

| Assessment time | Administration group | Number of cases analyzed | Score | | | |
|---|---|---|---|---|---|---|
| | | | 0 | 1 | 2 | 3 |
| Week 0 | Comparative Example 1 | 51 | 1 (2.0) | 13 (25.5) | 20 (39.2) | 17 (33.3) |
| | Example 1 | 51 | 2 (3.9) | 9 (17.6) | 21 (41.2) | 19 (37.3) |
| Week 2 | Comparative Example 1 | 51 | 4 (7.8) | 11 (21.6) | 18 (35.3) | 18 (35.3) |
| | Example 1 | 51 | 5 (9.8) | 13 (25.5) | 25 (49.0) | 8 (15.7) |
| Week 4 | Comparative Example 1 | 51 | 6 (11.8) | 12 (23.5) | 17 (33.3) | 16 (31.4) |
| | Example 1 | 51 | 6 (11.8) | 24 (47.1) | 13 (25.5) | 8 (15.7) |
| Week 8 | Comparative Example 1 | 51 | 4 (7.8) | 14 (27.5) | 15 (29.4) | 18 (35.3) |
| | Example 1 | 51 | 11 (21.6) | 23 (45.1) | 9 (17.6) | 8 (15.7) |

| Administration group | Assessment time | | Week 0 | | | |
|---|---|---|---|---|---|---|
| | | | 0 | 1 | 2 | 3 |
| Comparative Example 1 | Week 2 | 0 | 1 | 3 | 0 | 0 |
| | | 1 | 0 | 6 | 5 | 0 |
| | | 2 | 0 | 3 | 12 | 3 |
| | | 3 | 0 | 1 | 3 | 14 |
| | Week 4 | 0 | 1 | 2 | 2 | 1 |
| | | 1 | 0 | 6 | 5 | 1 |
| | | 2 | 0 | 4 | 8 | 5 |
| | | 3 | 0 | 1 | 5 | 10 |
| | Week 8 | 0 | 1 | 3 | 0 | 0 |
| | | 1 | 0 | 7 | 5 | 2 |
| | | 2 | 0 | 2 | 9 | 4 |
| | | 3 | 0 | 1 | 6 | 11 |
| Example 1 | Week 2 | 0 | 2 | 1 | 1 | 1 |
| | | 1 | 0 | 6 | 5 | 2 |
| | | 2 | 0 | 2 | 15 | 8 |
| | | 3 | 0 | 0 | 0 | 8 |

|  |  |  |  |  |  |
|---|---|---|---|---|---|
| Week 4 | 0 | 2 | 1 | 3 | 0 |
|  | 1 | 0 | 7 | 12 | 5 |
|  | 2 | 0 | 1 | 6 | 6 |
|  | 3 | 0 | 0 | 0 | 8 |
| Week 8 | 0 | 2 | 3 | 4 | 2 |
|  | 1 | 0 | 5 | 11 | 7 |
|  | 2 | 0 | 1 | 5 | 3 |
|  | 3 | 0 | 0 | 1 | 7 |

(7) Changes in Subscores for Bloody Stool of Mayo Scores

Figure 8:
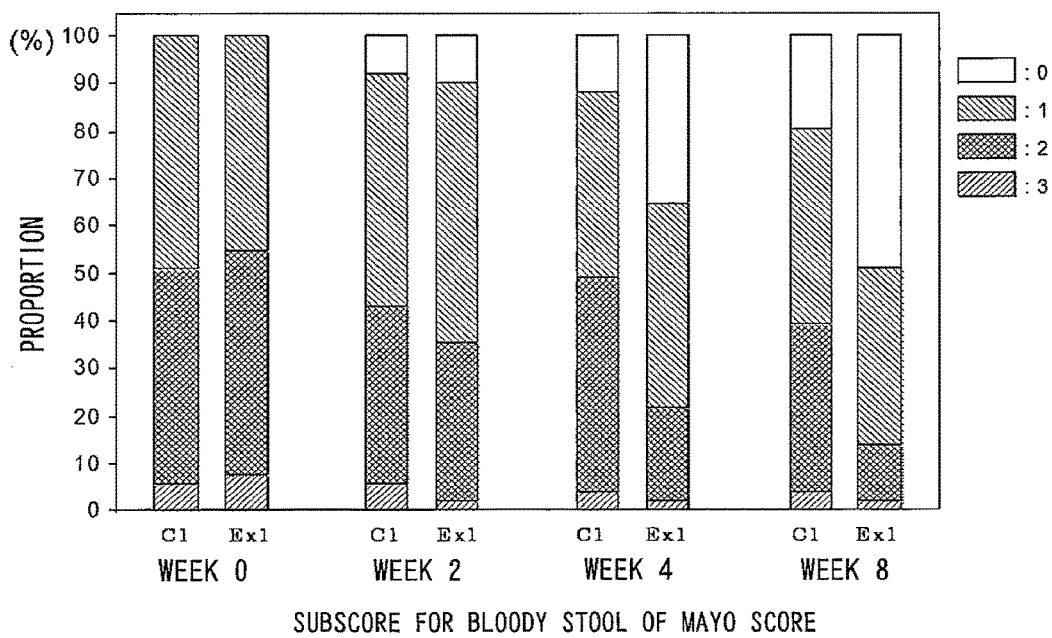
FIG. 8 is a graph showing changes in subscores for bloody stool of the administration groups in Example 1 and Comparative Example 1.

Table 12 shows a cross tabulation of the subscores for bloody stool of the Mayo scores, and FIG. 8 shows changes therein. Note that, in FIG. 8, C1 means Comparative Example 1, and Ex1 means Example 1.

(8) Changes in Subscores for Physician's Global Assessment of Mayo Scores

Figure 9:
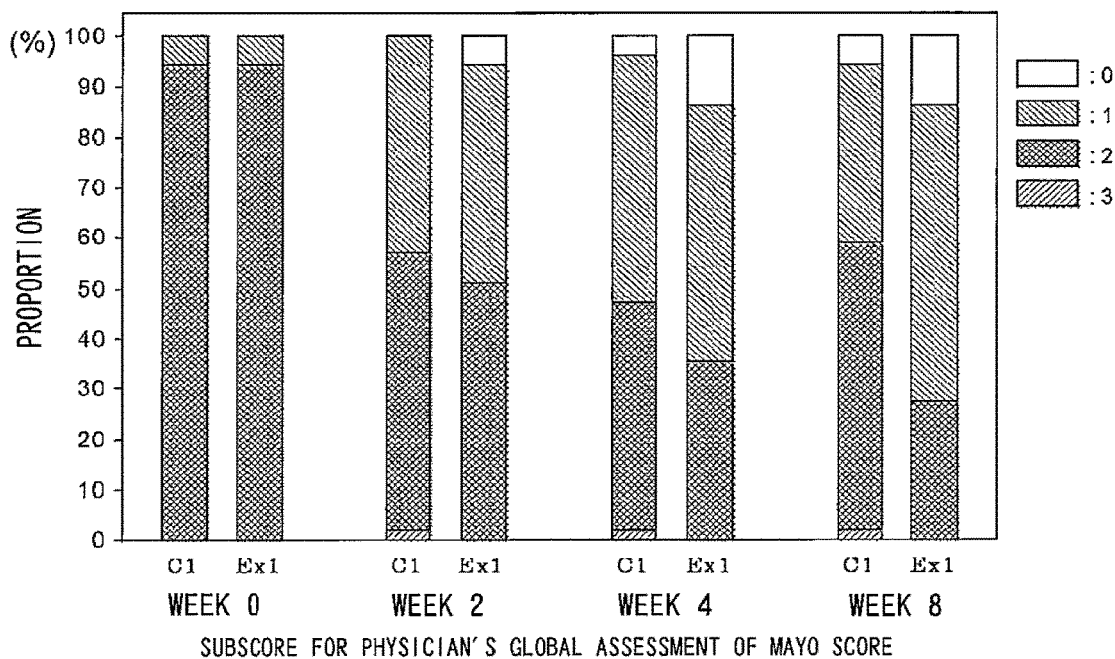
FIG. 9 is a graph showing changes in subscores for physician's global assessment of the administration groups in Example 1 and Comparative Example 1.

Table 13 shows a cross tabulation of the subscores for physician's global assessment of the Mayo scores, and FIG. 9 shows changes therein. Note that, in FIG. 9, C1 means Comparative Example 1, and Ex1 means Example 1.

| Assessment time | Administration group | Number of cases analyzed | Score 0 | 1 | 2 | 3 |
|---|---|---|---|---|---|---|
| Week 0 | Comparative Example 1 | 51 | — | 25 (49.0) | 23 (45.1) | 3 (5.9) |
|  | Example 1 | 51 | — | 23 (45.1) | 24 (47.1) | 4 (7.8) |
| Week 2 | Comparative Example 1 | 51 | 4 (7.8) | 25 (49.0) | 19 (37.3) | 3 (5.9) |
|  | Example 1 | 51 | 5 (9.8) | 28 (54.9) | 17 (33.3) | 1 (2.0) |
| Week 4 | Comparative Example 1 | 51 | 6 (11.8) | 20 (39.2) | 23 (45.1) | 2 (3.9) |
|  | Example 1 | 51 | 18 (35.3) | 22 (43.1) | 10 (19.6) | 1 (2.0) |
| Week 8 | Comparative Example 1 | 51 | 10 (19.6) | 21 (41.2) | 18 (35.3) | 2 (3.9) |
|  | Example 1 | 51 | 25 (49.0) | 19 (37.3) | 6 (11.8) | 1 (2.0) |

| Administration group | Assessment time |  | Week 0 1 | 2 | 3 |
|---|---|---|---|---|---|
| Comparative Example 1 | Week 2 | 0 | 4 | 0 | 0 |
|  |  | 1 | 17 | 7 | 1 |
|  |  | 2 | 3 | 15 | 1 |
|  |  | 3 | 1 | 1 | 1 |
|  | Week 4 | 0 | 5 | 1 | 0 |
|  |  | 1 | 14 | 6 | 0 |
|  |  | 2 | 5 | 16 | 2 |
|  |  | 3 | 1 | 0 | 1 |
|  | Week 8 | 0 | 6 | 4 | 0 |
|  |  | 1 | 11 | 10 | 0 |
|  |  | 2 | 7 | 9 | 2 |
|  |  | 3 | 1 | 0 | 1 |
| Example 1 | Week 2 | 0 | 2 | 2 | 1 |
|  |  | 1 | 18 | 8 | 2 |
|  |  | 2 | 3 | 14 | 0 |
|  |  | 3 | 0 | 0 | 1 |
|  | Week 4 | 0 | 9 | 8 | 1 |
|  |  | 1 | 12 | 9 | 1 |
|  |  | 2 | 2 | 7 | 1 |
|  |  | 3 | 0 | 0 | 1 |
|  | Week 8 | 0 | 13 | 9 | 3 |
|  |  | 1 | 8 | 11 | 0 |
|  |  | 2 | 2 | 4 | 0 |
|  |  | 3 | 0 | 0 | 1 |

| Administration group | Assessment time | | Week 0 | | | |
|---|---|---|---|---|---|---|
| | | | 0 | 1 | 2 | 3 |
| Comparative Example 1 | Week 2 | 0 | 0 | 0 | 0 | 0 |
| | | 1 | 0 | 3 | 19 | 0 |
| | | 2 | 0 | 0 | 28 | 0 |
| | | 3 | 0 | 0 | 1 | 0 |
| | Week 4 | 0 | 0 | 0 | 2 | 0 |
| | | 1 | 0 | 3 | 22 | 0 |
| | | 2 | 0 | 0 | 23 | 0 |
| | | 3 | 0 | 0 | 1 | 0 |
| | Week 8 | 0 | 0 | 0 | 3 | 0 |
| | | 1 | 0 | 3 | 15 | 0 |
| | | 2 | 0 | 0 | 29 | 0 |
| | | 3 | 0 | 0 | 1 | 0 |
| Example 1 | Week 2 | 0 | 0 | 0 | 3 | 0 |
| | | 1 | 0 | 3 | 19 | 0 |
| | | 2 | 0 | 0 | 26 | 0 |
| | | 3 | 0 | 0 | 0 | 0 |
| | Week 4 | 0 | 0 | 0 | 7 | 0 |
| | | 1 | 0 | 3 | 23 | 0 |
| | | 2 | 0 | 0 | 18 | 0 |
| | | 3 | 0 | 0 | 0 | 0 |
| | Week 8 | 0 | 0 | 1 | 6 | 0 |
| | | 1 | 0 | 2 | 28 | 0 |
| | | 2 | 0 | 0 | 14 | 0 |
| | | 3 | 0 | 0 | 0 | 0 |

(9) Bloody-Stool Disappearance Rate

Figure 10:
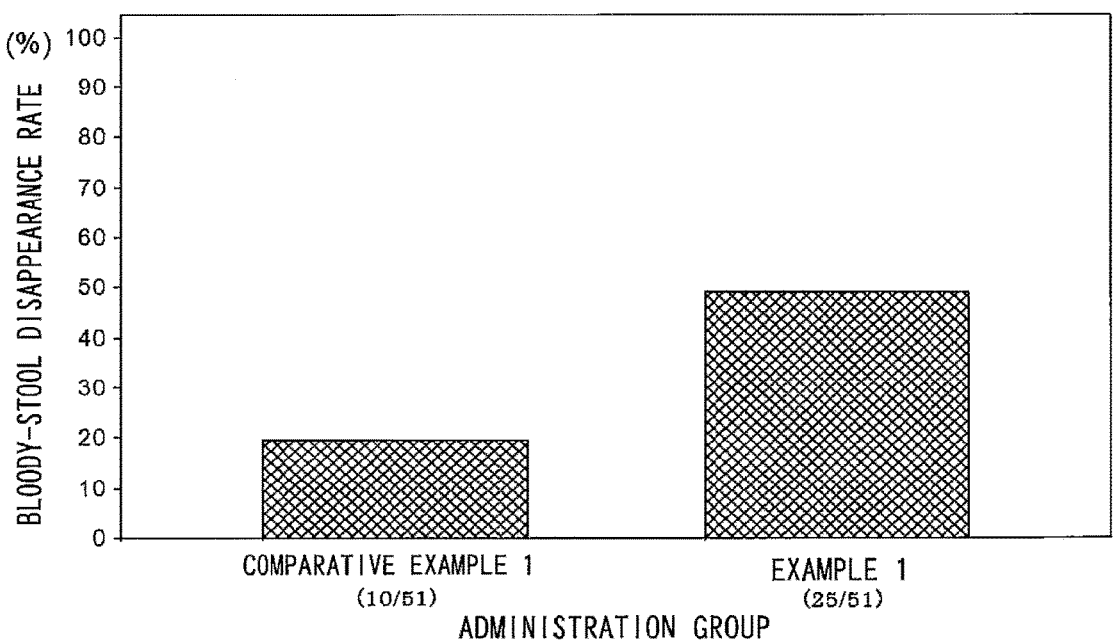
FIG. 10 is a graph showing bloody stool disappearance rates of the administration groups in Example 1 and Comparative Example 1.

Table 14 shows bloody-stool disappearance rates and an estimation of a difference in the bloody-stool disappearance rates, and FIG. 10 shows the bloody-stool disappearance rates.

The bloody-stool disappearance rate was 19.6% (10/51 cases) in Comparative Example 1 (placebo group), while that in Example 1 was 49.0% (25/51 cases). The difference between the two groups was 29.4%, and the two-sided 95% confidence interval was 11.0% to 45.2%.

| | | | | | Comparison of Example 1 with Comparative Example 1 | |
|---|---|---|---|---|---|---|
| Administration group | Number of cases analyzed | Bloody-stool disappearing cases | Bloody-stool disappearance rate (%) | 95% confidence interval | Difference in bloody-stool disappearance rates | 95% confidence interval of difference |
| Comparative Example 1 | 51 | 10 | 19.6 | 11.0 to 32.5 | — | — |
| Example 1 | 51 | 25 | 49.0 | 35.9 to 62.3 | 29.4 | 11.0 to 45.2 |

(10) Changes in Riley Scores (Histopathological Assessment)

At the time of the endoscopic examination on the large intestine for the mucosal finding assessment, large intestinal mucosal tissues were sampled (biopsy). The biopsy for the histopathological assessment at Week 0 was conducted during the endoscopic examination on the large intestine for the eligibility determination. The mucosal tissues around the most active sites were sampled, and mucosal tissues were sampled from the same sites at Week 8, too. The sampled tissues were fixed with formalin to prepare histopathological specimens.

The histopathological assessment was scored by a histopathological assessment central adjudication committee according to the following criteria. A Riley score is a total score of the following items.

| Assessment item | Score |
|---|---|
| Round cells of lamina propria | 0 to 3 |
| Polymorphonuclear cells of lamina propria | 0 to 3 |
| Crypt abscess | 0 to 3 |
| Decrease in mucosa | 0 to 3 |
| Integrity of surface epithelium | 0 to 3 |
| Abnormal crypt structure | 0 to 3 |

Table 16 shows descriptive statistics of the Riley scores, and FIG. 11 shows changes over time therein.

The Riley scores were 11.8±3.3 (mean±standard deviation) at Week 0 and 10.6±4.0 at Week 8 in Comparative Example 1 (placebo group), while those in Example 1 were 11.8±2.8 at Week 0 and 8.6±3.4 at Week 8. The difference in the mean between the groups at Week 8 was −1.96, and the two-sided 95% confidence interval was −3.55 to −0.38.

| | Administration group | Comparative Example 1 | Example 1 |
|---|---|---|---|
| Week 0 | Number of cases | 47 | 50 |
| | Mean | 11.8 | 11.8 |
| | Standard deviation | 3.3 | 2.8 |
| | Maximum | 17 | 17 |
| | Upper quartile | 14.0 | 14.0 |
| | Median | 12.0 | 12.0 |
| | Lower quartile | 10.0 | 9.0 |
| | Minimum | 4 | 6 |
| | Lower 95% confidence interval | 10.8 | 11.0 |
| | Upper 95% confidence interval | 12.7 | 12.6 |
| Week 8 | Number of cases | 40 | 46 |
| | Mean | 10.6 | 8.6 |
| | Standard deviation | 4.0 | 3.4 |
| | Maximum | 16 | 16 |
| | Upper quartile | 14.0 | 11.0 |
| | Median | 11.0 | 9.0 |
| | Lower quartile | 8.0 | 6.0 |
| | Minimum | 1 | 3 |
| | Lower 95% confidence interval | 9.3 | 7.6 |
| | Upper 95% confidence interval | 11.8 | 9.6 |

| Difference in mean between Example 1 and Comparative Example 1, and 95% confidence interval | | |
|---|---|---|
| Assessment timing | Mean | 95% confidence interval |
| week 8 | −1.96 | −3.55 to −0.38 |

<Adverse Event>

During the 8-week study period, no severe adverse event occurred. The incidence rate of moderate adverse events was 17.6% (9/51 cases) in Comparative Example 1 (placebo group), while that in Example 1 was 3.9% (2/51 cases). Comparative Example 1 (placebo group) had the higher incidence rate.

The causal relationship between any of the moderate adverse events and the study drug was denied. No moderate and severe adverse events having a causal relationship with the study drug occurred. All the other events were determined as mild.

<Discussion>

As a result of orally administering 960 mg of the compound of the formula (1) 3 times a day for 8 weeks to the ulcerative colitis patients in the active stage, the response rate at Week after the administration of study drug was started was significantly improved in comparison with Comparative Example (placebo). Similar results were obtained in the other secondary assessment items, too. The adverse event analysis also verified that there was no problem in safety.

INDUSTRIAL APPLICABILITY

The present invention makes it possible to effectively treat ulcerative colitis patients, particularly ulcerative colitis patients receiving a drug therapy of a 5-ASA preparation and/or a corticosteroid preparation.

The invention claimed is:

1. A method for treating ulcerative colitis, comprising administering a compound represented by formula (1) or a pharmaceutically acceptable salt thereof as an active ingredient in an amount of 1500 mg or more per day

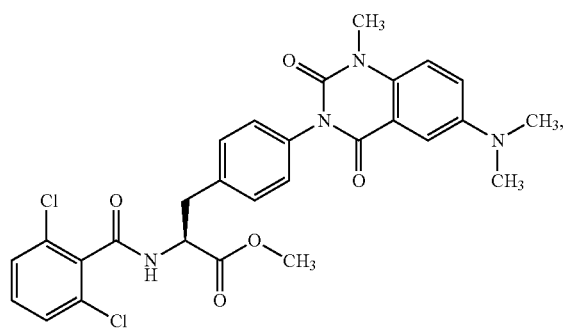

(1)

to an ulcerative colitis patient.

2. The method according to claim 1, wherein said compound or pharmaceutically acceptable salt is administered as an active ingredient in an amount of 1500 mg to 9000 mg per day to said ulcerative colitis patient.

3. The method according to claim 1, wherein said patient is an ulcerative colitis patient receiving a drug therapy of a 5-aminosalicylic acid preparation and/or a corticosteroid preparation.

4. The method according to claim 1, wherein said patient is an ulcerative colitis patient in an active stage on whom a drug therapy of a 5-aminosalicylic acid preparation and/or a corticosteroid preparation has an insufficient effect, or who is intolerant to the drug therapy.

5. The method according to claim 1, wherein said compound or pharmaceutically acceptable salt thereof is in the foul of an oral preparation.

6. The method according to claim 1, wherein said compound or pharmaceutically acceptable salt is administered 1 to 5 times a day.

7. The method according to claim 1, wherein said compound or pharmaceutically acceptable salt is administered 3 times a day at a dose of 500 mg or more per administration.

8. The method according to claim 7, wherein said compound or pharmaceutically acceptable salt is administered 3 times a day at a dose of 500 mg to 2000 mg per administration.

9. The method according to claim 1, wherein said compound or pharmaceutically acceptable salt is administered in an amount of 2500 to 3000 mg per day to said ulcerative colitis patient.

10. The method according to claim 9, wherein said compound or pharmaceutically acceptable salt is administered 3 times a day at a dose of 900 to 1000 mg per administration.

11. The method according to claim 10, wherein said patient is an ulcerative colitis patient in an active stage on whom a drug therapy of a 5-aminosalicylic acid preparation and/or a corticosteroid preparation has an insufficient effect.

* * * * *